(12) United States Patent
Gangjee

(10) Patent No.: US 8,314,114 B2
(45) Date of Patent: Nov. 20, 2012

(54) TRICYCLIC COMPOUNDS HAVING CYTOSTATIC AND/OR CYTOXIC ACTIVITY AND METHODS OF USE THEREOF

(75) Inventor: Aleem Gangjee, Allison Park, PA (US)

(73) Assignee: Duquesne University of The Holy Ghost, Pittsburgh, PA (US)

( * ) Notice: Subject to any disclaimer, the term of this patent is extended or adjusted under 35 U.S.C. 154(b) by 0 days.

(21) Appl. No.: 13/098,701

(22) Filed: May 2, 2011

(65) Prior Publication Data

US 2011/0207757 A1    Aug. 25, 2011

Related U.S. Application Data

(62) Division of application No. 11/845,143, filed on Aug. 27, 2007, now Pat. No. 7,960,400.

(51) Int. Cl.
*A01N 43/54* (2006.01)
*A61K 31/505* (2006.01)

(52) U.S. Cl. ............................................. 514/267
(58) Field of Classification Search ............ 514/267; 544/249, 250
See application file for complete search history.

(56) References Cited

U.S. PATENT DOCUMENTS

| | | | |
|---|---|---|---|
| 4,769,378 | A | 9/1988 | Hirsch et al. |
| 5,032,594 | A | 7/1991 | Takehiko et al. |
| 5,679,683 | A | 10/1997 | Bridges et al. |
| 6,596,726 | B1 | 7/2003 | Bridges et al. |
| 7,468,373 | B2 | 12/2008 | Heintzelman et al. |
| 2004/0127510 | A1 | 7/2004 | Heintzelman et al. |
| 2005/0267138 | A1 | 12/2005 | Heintzelman et al. |
| 2009/0082374 | A1 | 3/2009 | Gangjee |

FOREIGN PATENT DOCUMENTS

| WO | 03/037898 A1 | 5/2003 |
|---|---|---|
| WO | 2005/037825 A2 | 4/2005 |

OTHER PUBLICATIONS

Ngamga, et al., Millaurine and Acetylmillaurine: Alkaloids from *Millettia laurentii*, J. of Nat. Prod., vol. 56, No. 12, pp. 2126-2132 (1993).*
Supplementary European Search Report for EP Application No. 08828802.2 dated Mar. 18, 2011.
Nelson et al., "Dicyclic and Tricyclic Diaminopyrimidine Derivatives as Potent Inhibitors of *Cryptosporidium parvum* Dihydrofolate Reductase: Structure-Activity and Structure-Selectivity Correlations", Antimicrobial Agents and Chemotherapy, Dec. 1, 2001 American Society for Microbiology, Washington, DC, US—ISSN 0066-4804, vol. 45, No. 12, pp. 3293-3303.
Nelson et al. "Erratum: Dicyclic and Tricyclic Diaminopyrimidine Derivatives as Potent Inhibitors of *Cryptosporidium parvum* Dihydrofolate Reductase: Structure-Activity and Structure-Selectivity Correlations", Mar. 2002, Antimicrobial Agents and Chemotherapy, vol. 46, No. 3, p. 940.
Elslager et al., "Folate antagonists. 6. Synthesis and antimalarial effects of fused 2,4-diaminothieno[2,3-d] pyrimidines (1-3)", Journal of Heterocyclic Chemistry, Aug. 1972 Wiley-Blackwell Publishing, Inc, US—ISSN 0022-152X, vol. 9, pp. 775-782.
Rosowsky et al., "Synthesis of 2,4-diamino-9H-indeno[2,1-d]pyrimidines", Journal of Heterocyclic Chemistry, Oct. 1969 Wiley-Blackwell Publishing, Inc, US—ISSN 0022-152X, vol. 6, pp. 613-622.
International Search Report for PCT/US08/73824 dated Nov. 7, 2008 (PCT/ISA/220 and PCT/ISA/210).
Written Opinion of the International Searching Authority for PCT/US08/73824 dated Nov. 7, 2008 (PCT/ISA/237).
Ngama et al., Millaurine and Acetylmillaurine: Alkaloids from *Millettia laurentii*, J. of Nat. Prod. vol. 56, No. 12, pp. 2126-2132 (1993).
Rosowsky et al., Synthesis of 2,4-diamino-9H-indeno[2,1-d]pyrimidines, 6(5), 613-22, J. of Het. Chem (1969).

\* cited by examiner

*Primary Examiner* — Erich A Leeser
(74) *Attorney, Agent, or Firm* — Buchanan Ingersoll & Rooney PC; Craig G. Cochenour

(57) ABSTRACT

The present invention provides tricyclic compounds having cytostatic and cytotoxic activity in a single molecule having receptor tyrosine kinase(s), dihydrofolate reductase, thymidylate synthase and/or dihydroorotate dehydrogenase inhibitory activity, which are useful as anti-angiogenic and anti-tumor agents. Also provided are methods of utilizing these inhibitors to treat tumor cells and other proliferative diseases and disorders.

16 Claims, 11 Drawing Sheets

| | Formula | Calcd (%) | | | | | | Found % | | | | | |
|---|---|---|---|---|---|---|---|---|---|---|---|---|---|
| | | C | H | N | F | Cl | Br | C | H | N | F | Cl | Br |
| 4 | C$_{11}$H$_9$N$_3$O. 0.1H$_2$O | 65.73 | 4.61 | 20.94 | | | | 65.76 | 4.50 | 21.13 | | | |
| 12 | C$_{17}$H$_{13}$FN$_4$. 0.4H$_2$O | 68.17 | 4.64 | 18.71 | 6.34 | | | 68.36 | 4.47 | 18.42 | 6.40 | | |
| 13 | C$_{17}$H$_{13}$ClN$_4$ | 66.13 | 4.24 | 18.15 | | 11.48 | | 66.15 | 4.26 | 18.07 | | 11.56 | |
| 14 | C$_{17}$H$_{13}$BrN$_4$. 0.6CH$_3$OH | 56.76 | 4.17 | 15.04 | | | 21.45 | 56.95 | 3.93 | 15.16 | | | 21.21 |
| 15 | C$_{18}$H$_{13}$F$_3$N$_4$ | 63.16 | 3.83 | 16.37 | 16.65 | | | 62.78 | 3.81 | 16.21 | 16.51 | | |
| 19 | C$_{17}$H$_{12}$ClFN$_4$ | 62.49 | 3.70 | 17.15 | 5.81 | 10.85 | | 62.24 | 3.76 | 16.98 | 5.65 | 10.66 | |

Figure 10

TRICYCLIC COMPOUNDS HAVING CYTOSTATIC AND/OR CYTOXIC ACTIVITY AND METHODS OF USE THEREOF

BACKGROUND OF THE INVENTION

1. Field of the Invention

The present invention relates to tricyclic heteroaromatic compounds and their methods of use and, more particularly, to tricyclic heteroaromatic compounds that inhibit receptor tyrosine kinase(s), dihydrofolate reductase, thymidylate synthase and/or dihydroorotate dehydrogenase activity so as to exert cytostatic and cytotoxic action on tumor cells and other proliferative diseases and disorders.

2. Description of the Prior Art

The formation of new blood vessels from existing vasculature is termed angiogenesis. Angiogenesis plays a crucial role in the growth and metastasis of solid tumors. Solid tumors require angiogenesis to grow beyond 1-2 mm in diameter and metastasis requires the presence of blood vessels to allow access to the circulation and to form tumors at distal sites to the primary tumor. Angiogenesis and metastasis contribute to the poor prognosis in patients with angiogenic solid tumors. Thus, agents that inhibit the angiogenic process have afforded new paradigms for the treatment of tumors.

Angiogenesis primarily is a receptor-mediated process by growth factors that cause signal transduction, for the most part, by receptor tyrosine kinases (RTKs). RTKs consist of families of growth factor receptors such as vascular endothelial growth factor receptor (VEGFR), epidermal growth factor receptor (EGFR), platelet-derived growth factor receptor (PDGFR) and fibroblast growth factor receptor (FGFR). Aberrant expression or overexpression of EGFR and PDGFR, both of which are directly or indirectly involved in angiogenesis, have been implicated in the development, progression and aggressiveness of a variety of solid tumors. These include head and neck cancers (Shin, D. M. et al., Cancer Res., 54:3153-3159, 1994), non-small cell lung cancer (Tateishi, M. et al., Cancer Res., 50:7077-7080, 1990; Gorgoulis, V. et al., Anticancer Res., 12:1183-1187, 1992), glial tumors (Fleming, T. P. et al., Cancer Res., 52:4550-4553, 1992) and glioblastomas (Fleming, T. P. et al., Cancer Res., 52:4550-4553, 1992; Maxwell, M. et al., J. Clin. Invest., 86:131-140, 1990; Hermanson, M. et al., Cancer Res., 52:3213-3229, 1992).

Because RTKs are present in endothelial cells (VEGFR, PDGFR), tumor cells (FGFR, PDGFR) and pericytes/smooth muscle cells (FGFR, PDGFR), inhibition of more than one RTK may provide synergistic inhibitory effects against solid tumors. Thus, RTKs are attractive targets for cancer chemotherapeutic agents.

The importance of multiple RTK inhibition in angiogenesis is well recognized for the treatment of diseases such as cancer and macular degeneration, with multiple compounds in clinical use and several currently in various phases of clinical trials. These compounds, however, only are cytostatic, stopping the growth of tumors by blocking the angiogenesis pathway, and thus depriving tumors of the nutrition they need to grow. Hence, the antiangiogenic effect of these compounds does not kill tumor cells. To kill tumor cells, an additional cytotoxic effect is necessary. This cytotoxic effect can be provided by existing cancer chemotherapeutic agents. Thus, a variety of RTK inhibitors that are antiangiogenic and cytostatic have been combined with existing cancer chemotherapeutic agents that are cytotoxic, such as dihydrofolate reductase (DHFR) and thymidylate synthase (TS) inhibitors, in which DHFR and/or TS is the cytotoxic target. Preclinical and clinical trials of such combinations and other similar combinations have provided synergistic effects that are superior to either drug alone.

Preclinical studies also have shown that inhibition of multiple RTKs has shown an increase in survival of mice (Shaheen, R. M. et al., Cancer Res., 61:1464-1468, 2001). Thus, it is believed that the use of RTK inhibitors along with cytotoxic or conventional cancer chemotherapeutic agents and/or radiation enhances the efficacy of overall antitumor therapy and prevents regrowth following cessation of therapy (Dancey, J. et al., Nat. Rev. Drug Discov., 2:296-313, 2003; Kerbel, R. et al., Nat. Rev. Cancer, 2:727-739, 2002).

RTKs generally are transmembrane receptors consisting of an extracellular growth factor binding domain, a hydrophobic transmembrane domain, and a cytoplasmic domain. The cytoplasmic domain contains regulatory regions and a catalytic tyrosine kinase domain with a binding site for both ATP and substrates allowing for autophosphorylation, which is critical for signal transduction and angiogenesis.

Recently, VEGFR-2 and PDGFR-$\beta$, two RTKs, have been implicated in controlling angiogenesis at two different stages of the angiogenic process. In addition, inhibition of VEGFR-2 and PDGFR-$\beta$ with two separate inhibitors, SU5416 and SU6668, respectively, has been shown to produce a synergistic effect in early stage as well as late stage pancreatic islet cancer in mouse models by attacking the angiogenic process at two different sites (Bergers, G. et al., J. Clin. Invest., 111:1287-1295, 2003; Erber, R. et al., FASEB J., 18:338-340, 2004).

DHFR carries out the reduction of dihydrofolate to tetrahydrofolate (THF), which is utilized by serinehydroxymethyltransferase to produce 5,10-methylene-tetrahydrofolate (5,10-CH$_2$THF). The cofactor 5,10-CH$_2$THF serves as the source of the methyl group in the conversion of deoxyuridine monophosphate to thymidylate catalyzed by thymidylate synthase (TS). Both TS and DHFR inhibitors are well-established cytotoxic agents used in cancer chemotherapy (Gangjee, A. et al., Curr. Pharm. Des., 2:263-280, 1996). Methotrexate and trimetrexate are examples of such classical and non-classical antifolates, respectively, and 5-fluorouracil and pemetrexed are examples of TS inhibitors used clinically.

U.S. Pat. No. 5,679,683 discloses 4-substituted amino benzothieno[3,2-d]pyrimidine and 4-substituted pyrrolo[2,3-d] pyrimidine inhibitors of epidermal growth factor receptor family of tyrosines.

Showalter, H. D. H. et al. (J. Med. Chem., 42:5464-5474, 1999) disclose 6,5,6-tricyclic benzothienol[3,2-d]pyrimidines and pyrimido[5,4-b]- and -[4,5-b]indoles as inhibitors of epidermal growth factor receptor tyrosine kinases.

PCT published patent application No. WO2005/042500 discloses arylindenopyridines and arylindenopyridines and their use as an adenosine a2a receptor antagonist.

Gangjee, A. et al. (Bioorganic and Medicinal Chem., 13:5475-5491. 2005) disclose 5-substituted, 2,4-diaminofuro [2,3-d]pyrimidines as multireceptor tyrosine kinase and dihydrofolate reductase inhibitors with antiangiogenic and antitumor activity.

In general, it is highly desirable to develop new anti-angiogenic and anti-tumor compounds which inhibit both the formation of new blood vessels as well as selectively kill tumor cells. There is a need, therefore, for single compounds which provide the desired enzyme inhibition to achieve both cytostatic and cytotoxic activity with a high degree of selectivity and low toxicity.

SUMMARY OF THE INVENTION

The present invention meets the above need by providing single tricyclic compounds having cytostatic and cytotoxic activity in a single molecule so that significant drawbacks of different aspects of drug transport of two or more drugs to their targets, additive or synergistic toxicities of two or more different drugs, resistance of cancer cells to a particular drug, as well as the cost associated with two or more drugs, is circumvented.

It is an object of the present invention to provide single compounds that exhibit anti-angiogenic and anti-tumor activity in tumor cells, such as, without limitation, leukemia, non-small cell lung cancer, colon cancer, central nervous system cancer, melanoma, ovarian cancer, renal cancer, prostate cancer and breast cancer; and other proliferative diseases and disorders such as, without limitation, macular degeneration and retinopathies.

It is a further object of the present invention to provide single compounds that possess both cytostatic and cytotoxic activity in tumor cells and other proliferative diseases and disorders.

It is another object of the present invention to provide single compounds that possess both cytostatic and cytotoxic activity in tumor cells and other proliferative diseases and disorders by inhibiting activity against receptor tyrosine kinases (RTKs), dihydrofolate reductase (DHFR), thymidylate synthase (TS) and/or dihydroorotate dehydrogenase (DHODH).

It is another object of the present invention to provide single compounds that possess both cytostatic and cytotoxic activity in tumor cells and other proliferative diseases and disorders to overcome pharmacokinetic and pharmacodynamic drawbacks of drug transport of two or more separate agents to their targets.

It is another object of the present invention to provide single compounds that possess both cytostatic and cytotoxic activity in tumor cells and other proliferative diseases and disorders to overcome additive or synergistic combined toxicities of using two or more separate agents.

It is another object of the present invention to provide single compounds that possess both cytostatic and cytotoxic activity in tumor cells and other proliferative diseases and disorders to lessen the resistance of cancer cells to a particular drug.

It is another object of the present invention to provide single compounds that possess both cytostatic and cytotoxic activity in tumor cells and other proliferative diseases and disorders to overcome the cost associated with the use of two or more drugs.

It is another object of the present invention to provide methods of administering single compounds that possess both cytostatic and cytotoxic activity in tumor cells and other proliferative diseases and disorders.

The present invention fulfills the above objectives by providing single compounds having a combinatorial chemotherapeutic potential of both cytostatic and cytotoxic activity.

In an aspect of the present invention, there is provided a compound of formula I:

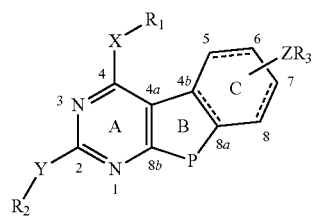

I wherein both B and C rings may be completely or partially saturated or unsaturated with respect to bond 4b-8a, 5-6 and 7-8; the C ring may have an N or substituted N depending on the saturation level of the C ring, and the substitution may be all of $R_1$, $R_2$ and $R_3$;

X and/or Y=N, NH, O, S, C; P=$NR_4$, O, S, $CR_4R_5$, wherein $R_4$ and $R_5$=lower alkyl, alkene, alkyne, and all of $R_1$ and $R_2$;

$R_1$ and/or $R_2$=H, alkyl, a cycloalkyl having 6 or less carbons, alkene, alkyne, carbonyl, aryl, heteroaryl, substituted aryl, substituted heteroaryl such as benzene, pyridine, biphenyl, bipyridine, quinazoline, isoquinoline, alkylaryl, alkylheteroaryl, substituted alkylaryl, alkylheteroaryl or a substituted or unsubstituted saturated heterocyclic having 6 or less atoms;

Z=S, O, $NR_5$, $CR_6R_7$, S—C, C—S, O—$CR_6$, $CR_6$—O, $NR_6$—C, C—$NR_6$, $CR_6$—$NR_7$ or $CR_6R_7$, wherein $R_5$, $R_6$, $R_7$=H or a lower alkyl, alkene, alkyne or cycloalkyl having 6 or less C atoms;

wherein Z may be attached to the C ring at positions 5, 6, 7 or 8 and may be the same or different and be attached to one or more positions on the ring;

wherein Z may be zero and $R_3$ may be directly attached to the C-ring at positions 5, 6, 7, and/or 8;

wherein when the C-ring is saturated or partially saturated the substituted Z or $R_3$ creates chirality when P=C and $R_6$ and $R_7$ are different, then all stereoisomers thereof both separately and as racemic and/or diastereoisomeric mixtures are included;

$R_3$=H, alkyl, cycloalkyl, aryl, heteroaryl, substituted aryl, substituted heteroaryl, alkylaryl, alkylheteroaryl and substituted saturated or unsaturated alkylheteroaryl and alkylheterocyclic, alkylaryl, p-, m-, o-benzoyl-L-glutamate or 2,5-, 2,4-thienoyl-L-glutamate when the benzene and thiophene ring may or may not have additional substitutions such as F, mono-, bi- and tricyclic aryl, heteroaryl or combinations thereof, ring substitutions such as biphenyl, bipyridyl or a phenyl-pyridyl or fused such as a quinoline or naphthyl including substituted systems such as a 2-chloro,4-biphenyl and tricyclic and substituted tricyclic systems.

In another aspect of the present invention, there is provided a compound of formula II:

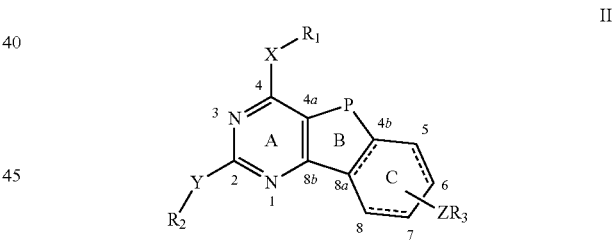

II wherein both B and C rings may be completely or partially saturated or unsaturated with respect to bond 4b-8a, 5-6 and 7-8; the C ring may have an N or substituted N depending on the saturation level of the C ring, and the substitution may be all of $R_1$, $R_2$ and $R_3$;

X and/or Y=N, NH, O, S, C; P=$NR_4$, O, S, $CR_4R_5$, wherein $R_4$ and $R_5$=lower alkyl, alkene, alkyne, and all of $R_1$ and $R_2$;

$R_1$ and/or $R_2$=H, alkyl, a cycloalkyl having 6 or less carbons, alkene, alkyne, carbonyl, aryl, heteroaryl, substituted aryl, substituted heteroaryl such as benzene, pyridine, biphenyl, bipyridine, quinazoline, isoquinoline, alkylaryl, alkylheteroaryl, substituted alkylaryl, alkylheteroaryl or a substituted or unsubstituted saturated heterocyclic having 6 or less atoms;

Z=S, O, $NR_5$, $CR_6R_7$, S—C, C—S, O—$CR_6$, $CR_6$—O, $NR_6$—C, C—$NR_6$, $CR_6$—$NR_7$ or $CR_6R_7$, wherein $R_5$, $R_6$, $R_7$=H or a lower alkyl, alkene, alkyne or cycloalkyl having 6 or less C atoms;

wherein Z may be attached to the C ring at positions 5, 6, 7 or 8 and may be the same or different and be attached to one or more positions on the ring;

wherein Z may be zero and $R_3$ may be directly attached to the C-ring at positions 5, 6, 7, and/or 8;

wherein when the C-ring is saturated or partially saturated the substituted Z or $R_3$ creates chirality when P=C and $R_6$ and $R_7$ are different, then all stereoisomers thereof both separately and as racemic and/or diastereoisomeric mixtures are included;

$R_3$=H, alkyl, cycloalkyl, aryl, heteroaryl, substituted aryl, substituted heteroaryl, alkylaryl, alkylheteroaryl and substituted saturated or unsaturated alkylheteroaryl and alkylheterocyclic, alkylaryl, p-, m-, o-benzoyl-L-glutamate or 2,5-, 2,4-thienoyl-L-glutamate when the benzene and thiophene ring may or may not have additional substitutions such as F, mono-, bi- and tricyclic aryl, heteroaryl or combinations thereof, ring substitutions such as biphenyl, bipyridyl or a phenyl-pyridyl or fused such as a quinoline or naphthyl including substituted systems such as a 2-chloro,4-biphenyl and tricyclic and substituted tricyclic systems.

In another aspect of the present invention, there is provided a method of inhibiting receptor tyrosine kinase(s), dihydrofolate reductase, thymidylate synthase and/or dihydroorotate dehydrogenase activity in an animal or human in need thereof, comprising administering to said animal or human a therapeutically effective amount in unit dosage form of a compound of formula I:

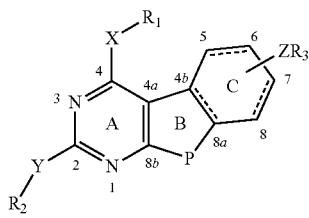

I wherein both B and C rings may be completely or partially saturated or unsaturated with respect to bond 4b-8a, 5-6 and 7-8; the C ring may have an N or substituted N depending on the saturation level of the C ring, and the substitution may be all of $R_1$, $R_2$ and $R_3$;

X and/or Y=N, NH, O, S, C; P=NR$_4$, O, S, CR$_4$R$_5$, wherein $R_4$ and $R_5$=lower alkyl, alkene, alkyne, and all of $R_1$ and $R_2$;

$R_1$ and/or $R_2$=H, alkyl, a cycloalkyl having 6 or less carbons, alkene, alkyne, carbonyl, aryl, heteroaryl, substituted aryl, substituted heteroaryl such as benzene, pyridine, biphenyl, bipyridine, quinazoline, isoquinoline, alkylaryl, alkylheteroaryl, substituted alkylaryl, alkylheteroaryl or a substituted or unsubstituted saturated heterocyclic having 6 or less atoms;

Z=S, O, NR$_S$, CR$_6$R$_7$, S—C, C—S, O—CR$_6$, CR$_6$—O, NR$_6$—C, C—NR$_6$, CR$_6$—NR$_7$ or CR$_6$R$_7$, wherein R$_5$, R$_6$, R$_7$=H or a lower alkyl, alkene, alkyne or cycloalkyl having 6 or less C atoms;

wherein Z may be attached to the C ring at positions 5, 6, 7 or 8 and may be the same or different and be attached to one or more positions on the ring;

wherein Z may be zero and $R_3$ may be directly attached to the C-ring at positions 5, 6, 7, and/or 8;

wherein when the C-ring is saturated or partially saturated the substituted Z or $R_3$ creates chirality when P=C and $R_6$ and $R_7$ are different, then all stereoisomers thereof both separately and as racemic and/or diastereoisomeric mixtures are included;

$R_3$=H, alkyl, cycloalkyl, aryl, heteroaryl, substituted aryl, substituted heteroaryl, alkylaryl, alkylheteroaryl and substituted saturated or unsaturated alkylheteroaryl and alkylheterocyclic, alkylaryl, p-, m-, o-benzoyl-L-glutamate or 2,5-, 2,4-thienoyl-L-glutamate when the benzene and thiophene ring may or may not have additional substitutions such as F, mono-, bi- and tricyclic aryl, heteroaryl or combinations thereof, ring substitutions such as biphenyl, bipyridyl or a phenyl-pyridyl or fused such as a quinoline or naphthyl including substituted systems such as a 2-chloro,4-biphenyl and tricyclic and substituted tricyclic systems.

In another aspect of the present invention, there is provided a method of inhibiting receptor tyrosine kinase(s), dihydrofolate reductase, thymidylate synthase and/or dihydroorotate dehydrogenase activity in an animal or human in need thereof, comprising administering to said animal or human a therapeutically effective amount in unit dosage form of a compound of formula II:

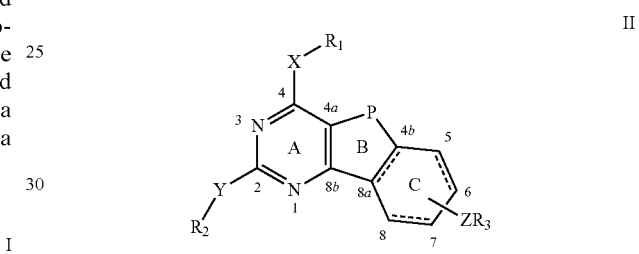

II wherein both B and C rings may be completely or partially saturated or unsaturated with respect to bond 4b-8a, 5-6 and 7-8; the C ring may have an N or substituted N depending on the saturation level of the C ring, and the substitution may be all of $R_1$, $R_2$ and $R_3$;

X and/or Y=N, NH, O, S, C; P=NR$_4$, O, S, CR$_4$R$_5$, wherein $R_4$ and $R_5$=lower alkyl, alkene, alkyne, and all of $R_1$ and $R_2$;

$R_1$ and/or $R_2$=H, alkyl, a cycloalkyl having 6 or less carbons, alkene, alkyne, carbonyl, aryl, heteroaryl, substituted aryl, substituted heteroaryl such as benzene, pyridine, biphenyl, bipyridine, quinazoline, isoquinoline, alkylaryl, alkylheteroaryl, substituted alkylaryl, alkylheteroaryl or a substituted or unsubstituted saturated heterocyclic having 6 or less atoms;

Z=S, O, NR$_5$, CR$_6$R$_7$, S—C, C—S, O—CR$_6$, CR$_6$—O, NR$_6$—C, C—NR$_6$, CR$_6$—NR$_7$ or CR$_6$R$_7$, wherein R$_5$, R$_6$, R$_7$=H or a lower alkyl, alkene, alkyne or cycloalkyl having 6 or less C atoms;

wherein Z may be attached to the C ring at positions 5, 6, 7 or 8 and may be the same or different and be attached to one or more positions on the ring;

wherein Z may be zero and $R_3$ may be directly attached to the C-ring at positions 5, 6, 7, and/or 8;

wherein when the C-ring is saturated or partially saturated the substituted Z or $R_3$ creates chirality when P=C and $R_6$ and $R_7$ are different, then all stereoisomers thereof both separately and as racemic and/or diastereoisomeric mixtures are included;

$R_3$=H, alkyl, cycloalkyl, aryl, heteroaryl, substituted aryl, substituted heteroaryl, alkylaryl, alkylheteroaryl and substituted saturated or unsaturated alkylheteroaryl and alkylheterocyclic, alkylaryl, p-, m-, o-benzoyl-L-glutamate or 2,5-, 2,4-thienoyl-L-glutamate when the benzene and thiophene ring may or may not have additional substitutions such as F, mono-, bi- and tricyclic aryl, heteroaryl or combinations thereof, ring substitutions such as biphenyl, bipyridyl or a phenyl-pyridyl or fused such as a quinoline or naphthyl including substituted systems such as a 2-chloro,4-biphenyl and tricyclic and substituted tricyclic systems.

BRIEF DESCRIPTION OF THE DRAWINGS

A full understanding of the invention can be gained from the following description of the preferred embodiments when read in conjunction with the accompanying drawings in which:

FIG. 7A is a graph of tumor volume.

FIG. 10 shows elemental analysis for Compounds 4, 12-15 and 19.

DESCRIPTION OF THE PREFERRED EMBODIMENTS

Figure 1:
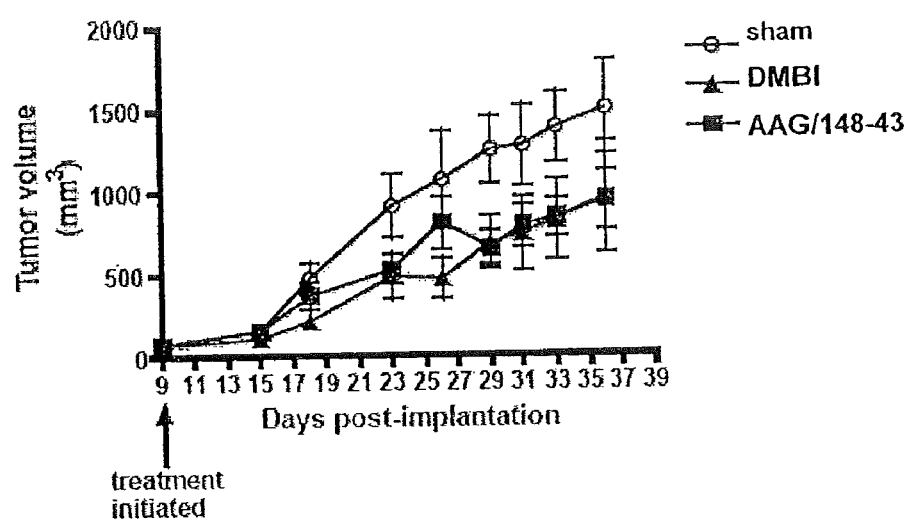
FIG. 1 illustrates primary tumor growth of COLO-205 metastatic human colon cancer cells implanted into the flank of athymic mice in response to DMBI (PDGFR kinase inhibitor) and AAG143-43 given at 25 mg/kg 3× weekly (M, W, F).

The present invention provides tricyclic compounds having cytostatic and cytotoxic activity in a single molecule having receptor tyrosine kinase(s) (RTK), dihydrofolate reductase (DHFR), thymidylate synthase (TS) and/or dihydroorotate dehydrogenase (DHODH) inhibitory activity and methods of use thereof.

In an embodiment of the present invention, there is provided a compound of formula I:

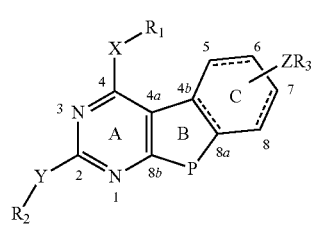

I wherein both B and C rings may be completely or partially saturated or unsaturated with respect to bond 4b-8a, 5-6 and 7-8; the C ring may have an N or substituted N depending on the saturation level of the C ring, and the substitution may be all of $R_1$, $R_2$ and $R_3$;

X and/or Y=N, NH, O, S, C; P=$NR_4$, O, S, $CR_4R_5$, wherein $R_4$ and $R_5$=lower alkyl, alkene, alkyne, and all of $R_1$ and $R_2$;

$R_1$ and/or $R_2$=H, alkyl, a cycloalkyl having 6 or less carbons, alkene, alkyne, carbonyl, aryl, heteroaryl, substituted aryl, substituted heteroaryl such as benzene, pyridine, biphenyl, bipyridine, quinazoline, isoquinoline, alkylaryl, alkylheteroaryl, substituted alkylaryl, alkylheteroaryl or a substituted or unsubstituted saturated heterocyclic having 6 or less atoms;

Z=S, O, $NR_5$, $CR_6R_7$, S—C, C—S, O—$CR_6$, $CR_6$—O, $NR_6$—C, C—$NR_6$, $CR_6$—$NR_7$ or $CR_6R_7$, wherein $R_5$, $R_6$, $R_7$=H or a lower alkyl, alkene, alkyne or cycloalkyl having 6 or less C atoms;

wherein Z may be attached to the C ring at positions 5, 6, 7 or 8 and may be the same or different and be attached to one or more positions on the ring;

wherein Z may be zero and $R_3$ may be directly attached to the C-ring at positions 5, 6, 7, and/or 8;

wherein when the C-ring is saturated or partially saturated the substituted Z or $R_3$ creates chirality when P=C and $R_6$ and $R_7$ are different, then all stereoisomers thereof both separately and as racemic and/or diastereoisomeric mixtures are included;

$R_3$=H, alkyl, cycloalkyl, aryl, heteroaryl, substituted aryl, substituted heteroaryl, alkylaryl, alkylheteroaryl and substituted saturated or unsaturated alkylheteroaryl and alkylheterocyclic, alkylaryl, p-, m-, o-benzoyl-L-glutamate or 2,5-, 2,4-thienoyl-L-glutamate when the benzene and thiophene ring may or may not have additional substitutions such as F, mono-, bi- and tricyclic aryl, heteroaryl or combinations thereof, ring substitutions such as biphenyl, bipyridyl or a phenyl-pyridyl or fused such as a quinoline or naphthyl including substituted systems such as a 2-chloro,4-biphenyl and tricyclic and substituted tricyclic systems.

A preferred form of formula I is where Y=NH; $R_2$=H; P=$NR_4$; $R_4$=H; X=NH; $R_1$=H; Z=S and $R_3$=a phenyl:

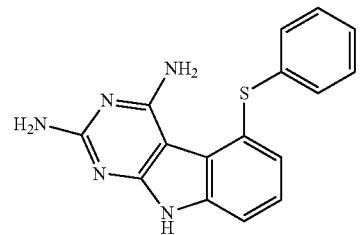

Another preferred form of formula I is where Y=NH; $R_2$=H; P=$CR_4R_5$; $R_4$=H; $R_5$=H; X=NH; $R_1$=a substituted aryl; Z=0; and $R_3$=H. The substitution on the aryl can be a halide, such as a chloride atom. A suitable ring structure is:

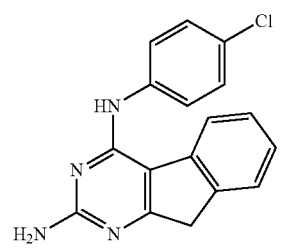

In another aspect of the present invention, there is provided a compound of formula II:

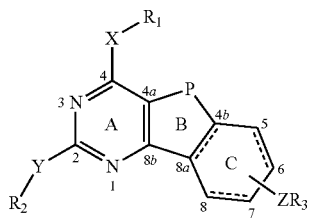

wherein both B and C rings may be completely or partially saturated or unsaturated with respect to bond 4b-8a, 5-6 and 7-8; the C ring may have an N or substituted N depending on the saturation level of the C ring, and the substitution may be all of $R_1$, $R_2$ and $R_3$;

X and/or Y=N, NH, O, S, C; P=$NR_4$, O, S, $CR_4R_5$, wherein $R_4$ and $R_5$=lower alkyl, alkene, alkyne, and all of $R_1$ and $R_2$;

$R_1$ and/or $R_2$=H, alkyl, a cycloalkyl having 6 or less carbons, alkene, alkyne, carbonyl, aryl, heteroaryl, substituted aryl, substituted heteroaryl such as benzene, pyridine, biphenyl, bipyridine, quinazoline, isoquinoline, alkylaryl, alkylheteroaryl, substituted alkylaryl, alkylheteroaryl or a substituted or unsubstituted saturated heterocyclic having 6 or less atoms;

Z=S, O, $NR_5$, $CR_6R_7$, S—C, C—S, O—$CR_6$, $CR_6$—O, $NR_6$—C, C—$NR_6$, $CR_6$—$NR_7$ or $CR_6R_7$, wherein $R_5$, $R_6$, $R_7$=H or a lower alkyl, alkene, alkyne or cycloalkyl having 6 or less C atoms;

wherein Z may be attached to the C ring at positions 5, 6, 7 or 8 and may be the same or different and be attached to one or more positions on the ring;

wherein Z may be zero and $R_3$ may be directly attached to the C-ring at positions 5, 6, 7, and/or 8;

wherein when the C-ring is saturated or partially saturated the substituted Z or $R_3$ creates chirality when P=C and $R_6$ and $R_7$ are different, then all stereoisomers thereof both separately and as racemic and/or diastereoisomeric mixtures are included;

$R_3$=H, alkyl, cycloalkyl, aryl, heteroaryl, substituted aryl, substituted heteroaryl, alkylaryl, alkylheteroaryl and substituted saturated or unsaturated alkylheteroaryl and alkylheterocyclic, alkylaryl, p-, m-, o-benzoyl-L-glutamate or 2,5-, 2,4-thienoyl-L-glutamate when the benzene and thiophene ring may or may not have additional substitutions such as F, mono-, bi- and tricyclic aryl, heteroaryl or combinations thereof, ring substitutions such as biphenyl, bipyridyl or a phenyl-pyridyl or fused such as a quinoline or naphthyl including substituted systems such as a 2-chloro,4-biphenyl and tricyclic and substituted tricyclic systems.

As used herein, the term "lower alkyl" group refers to those lower alkyl groups having one to about six carbon atoms, such as for example methyl, ethyl, propyl, butyl, pentyl, hexyl, cyclopropyl, cyclobutyl, cyclohexyl, cyclopropylmethyl or cyclobutylmethyl groups. Alkyl groups sharing one to about six carbon atoms are preferred. These lower alkyl groups are straight chain, branched chain or cyclic (alicyclic hydrocarbon) arrangements. The carbon atoms of these straight chain, branched chain or cyclic arranged alkyl groups may have one or more substituents for the hydrogens attached to the carbon atoms.

As used herein, the terms "heteroalkyl" and "heteroalkenyl" will be used to refer to alkyl or alkene chains from one to about 3 atoms where one or more of the carbons has been replaced with nitrogen, oxygen or sulfur. Thus "heteroalkyl" and "heteroalkenyl" groups will include, for example, C—C—N, C—S, S—C, C—O, C—C—O, O—C, N—C—C, N—C=C and other various combinations, as will be apparent to one skilled in the art. The above list is not meant to be exhaustive, and many combinations are contemplated as within the scope of the present invention.

"Aryl" groups, as used herein, will refer to compounds whose molecules have an aromatic ring structure, such as the six-carbon ring of benzene, or multiple rings which are either fused or unfused, such as condensed six-carbon rings of other aromatic derivatives. The term "aryl" is also defined to include diaryl, triaryl and polyaryl groups, which would have two, three or more rings, respectively. Thus, suitable aryl groups would include, for example, phenyl, biphenyl, naphthyl, phenanthrene, anthracene groups and aryl oxyaryl groups. This list is not meant to be exhaustive, and any aryl group, as these terms are defined above and commonly understood in the art, are within the scope of the present invention.

The term "heteroaryl", as used herein, will be used to refer to aromatic ring structures having at least one atom in the ring which is not carbon, such as oxygen, nitrogen or sulfur. "Heteroaryls" as used herein also refers to aromatic ring structures that are part of larger ring structures, such as two or three member ring systems, which may be fused or unfused, in which one of the rings is as described above. Thus, "heteroaryl" can refer to ring systems in which one or more rings contain a heteroatom and one or more rings do not. It will be understood that this list is not meant to be exhaustive, and that any heteroaryl group, as these terms are defined above and commonly understood in the art, are within the scope of the present invention. Examples include but are not limited to pyrroles, thiophenes, furans, imidazoles, and the like, as well as fused ring structures having rings of different sizes, such as benzofurans, indoles, purines, and the like.

Also included within the scope of the present invention are alicyclic groups, as that term is understood in the art, and heterocyclic groups. As used herein, the term "heterocyclic group" will refer to non-aromatic cyclic substituents in which one or more members of the ring is not carbon, for example oxygen, sulfur or nitrogen.

The terms "alkylaryl" (or "alkaryl") or "alkylheteroaryl" as used herein will refer to groups having an alkyl moiety attached to an aryl or heteroaryl ring. The alkyl moiety is preferably a straight, branched or cyclic alkyl group having one to about six carbon atoms. This alkyl moiety may also contain oxygen, nitrogen or sulfur atoms, and can therefore be an alkoxy group. The aryl or heteroaryl moiety of the alkylaryl group is a substituted or unsubstituted aryl or heteroaryl group, as these terms are described above. As used herein, the terms "alkylaryl" or "alkylheteroaryl" will also be used to refer to arylalkyl groups or heteroarylalkyl groups, as those terms are understood in the art, and will denote attachment of such a substituent at either the alkyl or the aryl portion of the group. Thus, for example, a benzyl group would be embraced by the term "alkylaryl".

Any of the cyclic substituents described above, such as the aryl, heteroaryl, alkylaryl, alkylheteroaryl, alicyclic, or heterocyclic groups are optionally substituted with one or more substituents as listed above. In the case of more than one substituent, the substituents are independently selected. "Alkoxy groups" and "alkyl groups" include straight or branched chains having up to about six members. "Halogen" refers to chlorine, bromine, iodine and fluorine. "Aryl and heteroaryl groups" are as described above. When a carboxylic acid is a substituent, it will be appreciated that the moiety represents an acid such as benzoic acid.

"Acyl" refers to an organic acid group in which the OH is replaced by some other substituent, and is generally designated as RCO— where R is a $C_{1-6}$ alkyl, $C_{2-6}$ alkenyl, or $C_{2-6}$ alkynyl straight or branched chain group.

As used herein, the terms "aroyl" or "heteroaroyl", such as when used within the term p-aroyl-L-glutamate, refers to benzoyl, napthoyl, thiophenoyl, furophenoyl, pyrroyl, and any other "aroyl" or "heteroaroyl" as these terms would be understood by one skilled in the art. "Aroyl" and "heteroaroyl" are generally defined in the art as an aromatic or heteroaromatic compound having a carbonyl moiety. "Glutamate" will be understood as representing both the ester form (glutamate) and the acid form (glutamic acid).

It will appreciated by those skilled in the art that a general formula depicting compounds having side chains with adjacent carbons having a double bond will result in both cis and trans isomers as possible structures. Both the cis and trans isomers, and mixtures thereof, of any such compound within the broad general formula described in formulas I and II are contemplated as being within the present invention.

A preferred form of formula II is where Y=NH; $R_2$=H; P=$CR_4R_5$; $R_4$=H; $R_5$=H; X=NH; $R_1$=phenyl; Z=O; and $R_3$=H:

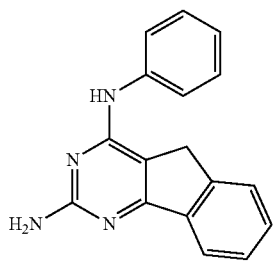

In another embodiment of the present invention, there is provided a method of inhibiting receptor tyrosine kinase(s), dihydrofolate reductase, thymidylate synthase and/or dihydroorotate dehydrogenase activity in an animal or human in need thereof, comprising administering to said animal or human a therapeutically effective amount in unit dosage form of a compound of formula I:

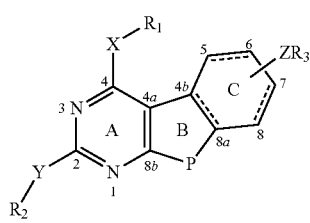

wherein both B and C rings may be completely or partially saturated or unsaturated with respect to bond 4b-8a, 5-6 and 7-8; the C ring may have an N or substituted N depending on the saturation level of the C ring, and the substitution may be all of $R_1$, $R_2$ and $R_3$;

X and/or Y=N, NH, O, S, C; P=$NR_4$, O, S, $CR_4R_5$, wherein $R_4$ and $R_5$=lower alkyl, alkene, alkyne, and all of $R_1$ and $R_2$;

$R_1$ and/or $R_2$=H, alkyl, a cycloalkyl having 6 or less carbons, alkene, alkyne, carbonyl, aryl, heteroaryl, substituted aryl, substituted heteroaryl such as benzene, pyridine, biphenyl, bipyridine, quinazoline, isoquinoline, alkylaryl, alkylheteroaryl, substituted alkylaryl, alkylheteroaryl or a substituted or unsubstituted saturated heterocyclic having 6 or less atoms;

Z=S, O, $NR_5$, $CR_6R_7$, S—C, C—S, O—$CR_6$, $CR_6$—O, $NR_6$—C, C—$NR_6$, $CR_6$—$NR_7$ or $CR_6R_7$, wherein $R_5$, $R_6$, $R_7$=H or a lower alkyl, alkene, alkyne or cycloalkyl having 6 or less C atoms;

wherein Z may be attached to the C ring at positions 5, 6, 7 or 8 and may be the same or different and be attached to one or more positions on the ring;

wherein Z may be zero and $R_3$ may be directly attached to the C-ring at positions 5, 6, 7, and/or 8;

wherein when the C-ring is saturated or partially saturated the substituted Z or $R_3$ creates chirality when P=C and $R_6$ and $R_7$ are different, then all stereoisomers thereof both separately and as racemic and/or diastereoisomeric mixtures are included;

$R_3$=H, alkyl, cycloalkyl, aryl, heteroaryl, substituted aryl, substituted heteroaryl, alkylaryl, alkylheteroaryl and substituted saturated or unsaturated alkylheteroaryl and alkylheterocyclic, alkylaryl, p-, m-, o-benzoyl-L-glutamate or 2,5-, 2,4-thienoyl-L-glutamate when the benzene and thiophene ring may or may not have additional substitutions such as F, mono-, bi- and tricyclic aryl, heteroaryl or combinations thereof, ring substitutions such as biphenyl, bipyridyl or a phenyl-pyridyl or fused such as a quinoline or naphthyl including substituted systems such as a 2-chloro,4-biphenyl and tricyclic and substituted tricyclic systems.

Proliferative diseases and/or disorders that may be treated according to the methods of the present invention include, without limitation, leukemia, non-small cell lung cancer, colon cancer, central nervous system cancer, melanoma, ovarian cancer, renal cancer, prostate cancer, breast cancer; macular degeneration and retinopathies.

A preferred form of formula I is where Y=NH; $R_2$=H; P=$NR_4$; $R_4$=H; X=NH; $R_1$=H; Z=S and $R_3$=a phenyl:

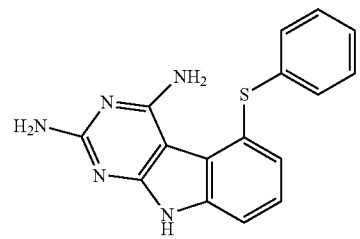

Another preferred form of formula I is where Y=NH; $R_2$=H; P=$CR_4R_5$; $R_4$=H; $R_5$=H; X=NH; $R_1$=a substituted aryl; Z=O; and $R_3$=H. The substitution on the aryl can be a halide, such as a chloride atom. A suitable ring structure is:

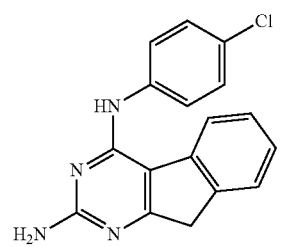

In another embodiment of the present invention, there is provided a method of inhibiting receptor tyrosine kinase(s), dihydrofolate reductase, thymidylate synthase and/or dihydroorotate dehydrogenase activity in an animal or human in need thereof, comprising administering to said animal or human a therapeutically effective amount in unit dosage form of a compound of formula II:

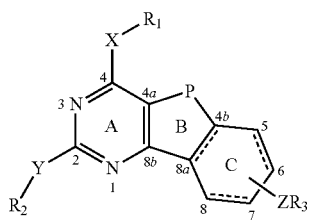

wherein both B and C rings may be completely or partially saturated or unsaturated with respect to bond 4b-8a, 5-6 and 7-8; the C ring may have an N or substituted N depending on the saturation level of the C ring, and the substitution may be all of $R_1$, $R_2$ and $R_3$;

X and/or Y=N, NH, O, S, C; P=$NR_4$, O, S, $CR_4R_5$, wherein $R_4$ and $R_5$=lower alkyl, alkene, alkyne, and all of $R_1$ and $R_2$;

$R_1$ and/or $R_2$=H, alkyl, a cycloalkyl having 6 or less carbons, alkene, alkyne, carbonyl, carbonyl, aryl, heteroaryl, substituted aryl, substituted heteroaryl such as benzene, pyridine, biphenyl, bipyridine, quinazoline, isoquinoline, alkylaryl, alkylheteroaryl, substituted alkylaryl, alkylheteroaryl or a substituted or unsubstituted saturated heterocyclic having 6 or less atoms;

Z=S, O, $NR_5$, $CR_6R_7$, S—C, C—S, O—$CR_6$, $CR_6$—O, $NR_6$—C, C—$NR_6$, $CR_6$—$NR_7$ or $CR_6R_7$, wherein $R_5$, $R_6$, $R_7$=H or a lower alkyl, alkene, alkyne or cycloalkyl having 6 or less C atoms;

wherein Z may be attached to the C ring at positions 5, 6, 7 or 8 and may be the same or different and be attached to one or more positions on the ring;

wherein Z may be zero and $R_3$ may be directly attached to the C-ring at positions 5, 6, 7, and/or 8;

wherein when the C-ring is saturated or partially saturated the substituted Z or $R_3$ creates chirality when P=C and $R_6$ and $R_7$ are different, then all stereoisomers thereof both separately and as racemic and/or diastereoisomeric mixtures are included;

$R_3$=H, alkyl, cycloalkyl, aryl, heteroaryl, substituted aryl, substituted heteroaryl, alkylaryl, alkylheteroaryl and substituted saturated or unsaturated alkylheteroaryl and alkylheterocyclic, alkylaryl, p-, m-, o-benzoyl-L-glutamate or 2,5-, 2,4-thienoyl-L-glutamate when the benzene and thiophene ring may or may not have additional substitutions such as F, mono-, bi- and tricyclic aryl, heteroaryl or combinations thereof, ring substitutions such as biphenyl, bipyridyl or a phenyl-pyridyl etc. or fused such as a quinoline or naphthyl including substituted systems such as a 2-chloro,4-biphenyl and tricyclic and substituted tricyclic systems.

A preferred form of formula II is where Y=NH; $R_2$=H; P=$CR_4R_5$; $R_4$=H; R5=H; X=NH; $R_1$=phenyl; Z=0; and $R_3$=H:

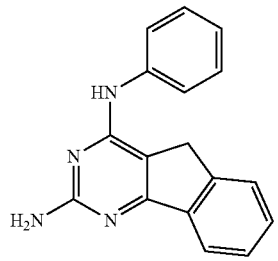

As used herein, the term "patient" means adult members of the animal kingdom, including, but not limited to, human beings.

As used herein, the term "therapeutically effective amount" refers to that amount of any of the present compounds required to bring about a desired effect in a patient. The desired effect will vary depending on the illness being treated. For example, the desired effect may be reducing tumor size, destroying cancerous cells, preventing metastasis or reducing symptoms associated with the various other diseases listed above and contemplated as being within the treatment methods of the present invention. On its most basic level, a therapeutically effective amount is that amount needed to inhibit the activity of receptor tyrosine kinase(s) generally and/or dihydrofolate reductase and/or thymidylate synthase and/or dihydroorotate dehydrogenase. Any amount of inhibition will yield a benefit to a patient and is therefore within the scope of the invention.

It is especially advantageous to formulate parenteral compositions in dosage unit form for ease of administration and uniformity of dosage. Dosage unit form as used herein refers to physically discrete units suited as unitary dosages for the patients being treated, each unit containing a predetermined quantity or effective amount of a tricyclic compound to produce the desired effect in association with a pharmaceutical carrier. The specification for the dosage unit forms of the invention are dictated by and directly dependent on the particular compound and the particular effect to be achieved.

Compounds containing formula I or formula II can be administered to an animal or human via various routes including parenterally, orally or intraperitoneally. Parenteral administration includes the following routes: intravenous; intramuscular; interstitial, intraarterial; subcutaneous; intraocular; intracranial; intraventricular; intrasynovial; transepithelial, including transdermal, pulmonary via inhalation, ophthalmic, sublingual and buccal; topical, including dermal, ocular, rectal, or nasal inhalation via insufflation or nebulization.

Compounds containing formula I or formula II that are orally administered can be enclosed in hard or soft shell gelatin capsules, or compressed into tablets. Compounds also can be incorporated with an excipient and used in the form of ingestible tablets, buccal tablets, troches, capsules, sachets, lozenges, elixirs, suspensions, syrups, wafers and the like. Compounds containing formula I or formula II can be in the form of a powder or granule, a solution or suspension in an aqueous liquid or non-aqueous liquid, or in an oil-in-water emulsion.

The tablets, troches, pills, capsules and the like also can contain, for example, a binder, such as gum tragacanth, acacia, corn starch; gelating excipients, such as dicalcium phosphate; a disintegrating agent, such as corn starch, potato starch, alginic acid and the like; a lubricant, such as magnesium stearate; a sweetening agent, such as sucrose, lactose or saccharin; or a flavoring agent. When the dosage unit form is a capsule, it can contain, in addition to the materials described above, a liquid carrier. Various other materials can be present as coatings or to otherwise modify the physical form of the dosage unit. For example, tablets, pills, or capsules can be coated with shellac, sugar or both. A syrup or elixir can contain the active compound, sucrose as a sweetening agent, methyl and propylparabens as preservatives, a dye and flavoring. Any material used in preparing any dosage unit form should be pharmaceutically pure and substantially non-toxic. Additionally, the compounds of formula I or formula II can be incorporated into sustained-release preparations and formulations.

The compounds of formula I or formula II can be administered to the central nervous system, parenterally or intraperitoneally. Solutions of the compound as a free base or a pharmaceutically acceptable salt can be prepared in water mixed with a suitable surfactant, such as hydroxypropylcellulose. Dispersions also can be prepared in glycerol, liquid polyethylene glycols and mixtures thereof, and in oils. Under ordinary conditions of storage and use, these preparations can contain a preservative and/or antioxidants to prevent the growth of microorganisms or chemical degeneration.

The pharmaceutical forms suitable for injectable use include, without limitation, sterile aqueous solutions or dispersions and sterile powders for the extemporaneous preparation of sterile injectable solutions or dispersions. In all cases, the form must be sterile and must be fluid to the extent that easy syringability exists. It can be stable under the conditions of manufacture and storage and must be preserved against the contaminating action of microorganisms, such as bacteria and fungi. The carrier can be a solvent or dispersion medium which contains, for example, water, ethanol, polyol (such as propylene glycol and liquid polyethylene glycol), suitable mixtures thereof, or vegetable oils. The proper fluidity can be maintained, for example, by the use of a coating, such as lecithin, by the maintenance of the required particle size (in the case of a dispersion) and by the use of surfactants. The prevention of the action of microorganisms can be brought about by various antibacterial and anti-fungal agents, for example, parabens, chlorobutanol, phenol, sorbic acid, thimerosal, and the like. In many cases, it will be preferable to include isotonic agents, for example, sugars or sodium chloride.

Sterile injectable solutions are prepared by incorporating the compound of formula I or formula II in the required amount in the appropriate solvent with various of the other ingredients enumerated above, as required, followed by filtered sterilization. Generally, dispersions are prepared by incorporating the sterilized compound of formula I or formula II into a sterile vehicle that contains the basic dispersion medium and any of the other ingredients from those enumerated above. In the case of sterile powders for the preparation of sterile injectable solutions, the preferred methods of preparation are vacuum drying and freeze drying.

Pharmaceutical compositions which are suitable for administration to the nose and buccal cavity include, without limitation, self-propelling and spray formulations, such as aerosol, atomizers and nebulizers.

The therapeutic compounds of formula I and formula II can be administered to an animal or human alone or in combination with pharmaceutically acceptable carriers or as pharmaceutically acceptable salts, the proportion of which is determined by the solubility and chemical nature of the compound, chosen route of administration and standard pharmaceutical practice.

The compounds of the present invention are distinguished from prior art compounds in that the inventive compounds disclosed herein have substituents on the C-ring which are either halogens such as chloro, bromo, iodo and fluoro; L-glutamate-bearing side chains; aryl (directly connected); or one atom linked aryl of the type: thioaryl; aminoaryl; oxoaryl; carboaryl; compounds in which the C-ring is partially substituted; compounds of the type in which the B-ring is cyclopentane; compounds in which the substituents on the B-ring are either aryl or methyl aryl (e.g., benzyl).

The present invention is more particularly described in the following non-limiting examples, which are intended to be illustrative only, as numerous modifications and variations therein will be apparent to those skilled in the art.

EXAMPLES

Example 1

Compounds Derived from Compound of Formula I

1. AAG148-43 Efficacy in an Animal Model of Cancer

Single compounds which possess both antiangiogenic, i.e., cytostatic, activity and cytotoxic activity were designed, synthesized and evaluated. COLO-205 metastatic human colon cancer cells were implanted in mice. AAG-148-43 was administered to the mice at a dose of 25 mg/kg three times a week. FIG. 1 shows the antitumor activity of AAG-148-43 compared to DMBI (a standard PDGFR-β inhibitor). AAG-148-43 significantly reduced the growth of COLO-205 metastatic human colon cancer cells in mice comparable to the reduction observed in the standard PDGFR-β inhibitor.

As shown in Table 1, the cytotoxic activity of the compounds resulted in the inhibition of VEGFR-2 and PDGFR-β at levels comparable to standards SU5416 and DMBI, respectively. For AAG-148-43 and AAG-148-311, the RTK inhibitory activity (PDGFR-β) activity was compared to the standard DMBI.

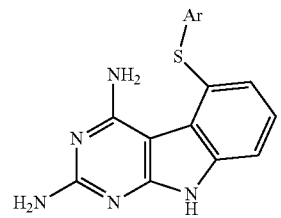

TABLE 1

| Compound # | ID | Ar |
|---|---|---|
| 1 | AAG148-43 | Ph |
| 2 | AAG148-311 | 4-MePh |

RTK Inhibitory activity
IC$_{50}$ values (μM) of kinase inhibition and A431 cytotoxicity assay

| Compd # | EGFR kinase inhibition | VEGFR-2 kinase inhibition | PDGFR-β kinase inhibition | A431 cytotoxicity |
|---|---|---|---|---|
| AAG-148-43 | 15.07 | 22.6 | 2.8 | 49.2 |
| PD153035 | 0.23 | | | |
| SU5416 | | 12.9 | | |
| DMBI | | | 3.75 | |
| Cisplatin | | | | 10.6 |

As shown in Table 2, the cytotoxic activity resulted in the inhibition of enzyme(s) in the folate metabolic pathway such as thymidylate synthase (TS). The TS inhibitory activity was compared to the standard PDDF. AAG-148-43 was a preferred embodiment, having shown multi-RTK (VEGF-2 and PDGFR-β) (cytostatic) inhibitory activity as well as TS (cytotoxic) inhibitory activity.

TABLE 2

TS inhibitory activity
$IC_{50}$ values (μM) of Thymidylate Synthase inhibition

| Compd # | Human | E. coli | Toxo |
|---|---|---|---|
| AAG-148-43 | 0.54 | >27 (36) | 0.11 |
| AAG-148-311 | 0.39 | >26 (34) | 0.18 |
| PDDF | 0.06 | 0.06 | 0.06 |
| Pemetrexed | 29 | 15 | 14 |
| Raltitrexed | .29 | 2.3 | 0.48 |

Figure 2:
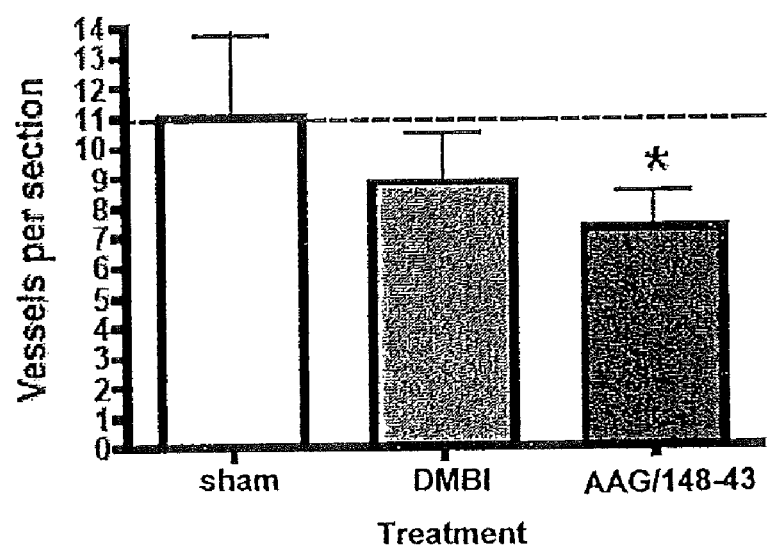
FIG. 2 illustrates vascularity of COLO-205 primary tumors in athymic mice in response to DMBI (PDGFR kinase inhibitor) and AAG148-43 given at 25 mg/kg 3× weekly (M, W, F).

FIG. 2 shows the reduction of vascularity of primary tumors with AAG-148-43 compared to DMBI and untreated animals. AAG-148-43 reduced vascularity much better than DMBI, and thus demonstrated its potent antiangiogenic activity in tumors in an animal model of cancer.

Figure 3:
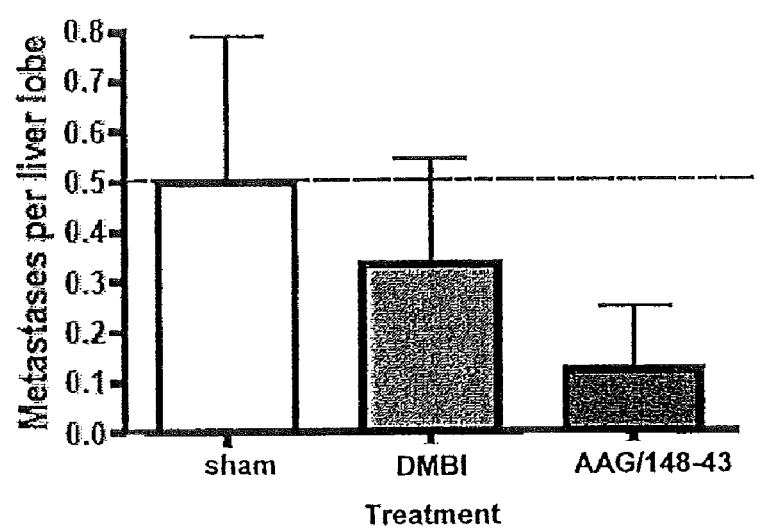
FIG. 3 illustrates metastasis to the liver of COLO-205 cells implanted into athymic mice in response to DMBI (PDGFR kinase inhibitor) and AAG148-43 given at 25 mg/kg 3× weekly (M, W, F).

COLO-205 cells were implanted into athymic mice. FIG. 3 shows metastasis to the liver of the COLO-205 cells in response to administration of AAG-148-43, DMBI and untreated mice. AAG-148-43 significantly reduced metastasis to the liver compared to DMBI and the untreated animals, demonstrating the ability of AAG-148-43 to significantly inhibit metastasis.

The above-described results demonstrate the significantly better overall outcome for reduction of tumor growth, reduction of vascularity and reduction of metastasis with AAG-148-43 of this series compared to the standard and the untreated mice. In addition, AAG-148-43 administration caused no apparent toxicity (no loss in weight of the animals) at a dose of 25 mg/kg three times weekly.

2. Compound 3 Efficacy in an Animal Model of Cancer

The structure of Compound 3 (AAG145-136; Table 3) is as follows:

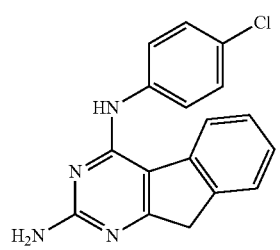

wherein Formula I has the following substitutions: $P=CH_2$; $R_3=H$; $X=NH$; $Y=NH_2$; and $R_1=p-ClC_6H_4$.

Compound 3 was shown to have potent multi-RTK inhibitory activity in EGFR and PDGFR-β along with A431 cytotoxicity and inhibition of angiogenesis in a CAM assay (Table 3).

TABLE 3

$IC_{50}$ value (μM) of kinase inhibition, A431 cytotoxicity and inhibition of CAM assay

| Compound | EGFR kinase | Flk-1 kinase | Flt-1 kinase | PDGFR-β kinase | A431 cytotoxicity | CAM angiogenesis |
|---|---|---|---|---|---|---|
| AAG145-124 | >200 | >200 | | 21.7 | 126.4 | 2.12 |
| AAG145-126 | 42.6 | 11.0 | | 7.8 | 126.4 | 14.8 |

TABLE 3-continued
IC$_{50}$ value (μM) of kinase inhibition, A431 cytotoxicity and inhibition of CAM assay
| Compound | EGFR kinase | Flk-1 kinase | Flt-1 kinase | PDGFR-β kinase | A431 cytotoxicity | CAM angiogenesis |
|---|---|---|---|---|---|---|
| AAG145-131 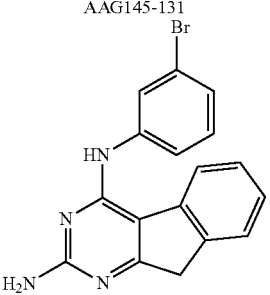 | 24.1 | >200 | | 126.3 | >5000 | 104.3 |
| AAG145-135 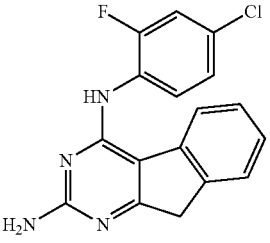 | 11.7 | 197.1 | | 3.6 | 9.7 | 3.67 |
| AAG145-136 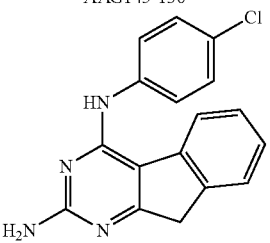 | 26.0 | >200 | | 0.8 | 9.7 | 0.82 |
| AAG145-157 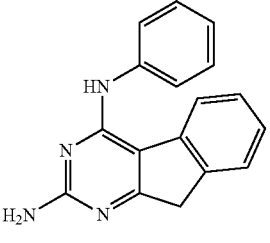 | 19.6 | 133.9 | | >500 | 235.0 | |
| SU5416 | | 10.6 | | | 19.2 ± 4.2 | 0.032 ± 0.005 |
| PD153035 | 0.23 | | | | | |
| PD168393 | 0.13 | | | | | |
| cisplatin | | | | | 10.6 | |
| DMBI | | | | 3.75 | | |
| VEGF inhibitor | | | 11.9 | | | |

TABLE 3-continued

IC$_{50}$ value (μM) of kinase inhibition, A431 cytotoxicity and inhibition of CAM assay

| Compound | EGFR kinase | Flk-1 kinase | Flt-1 kinase | PDGFR-β kinase | A431 cytotoxicity | CAM angiogenesis |
|---|---|---|---|---|---|---|
| AAG145-158 | >200 | 171.2 | | 43.1 | 4.9 | 50.8 |
| AAG145-159 | >200 | 43.0 | | 75.5 | 13.9 | |
| AAG145-161 | >200 | 55.7 | | 7.1 | 9.8 | 78.3 |
| AAG145-164 | >200 | 72.9 | | 6.4 | 158.1 | |
| SU5416 | | 10.6 | | | 19.2 ± 4.2 | 0.032 ± 0.005 |
| PD153035 | 0.23 | | | | | |
| PD168393 | 0.13 | | | | | |
| cisplatin | | | | | 10.6 | |
| DMBI | | | | 3.75 | | |
| VEGF inhibitor | | 11.9 | | | | |

Figure 4:
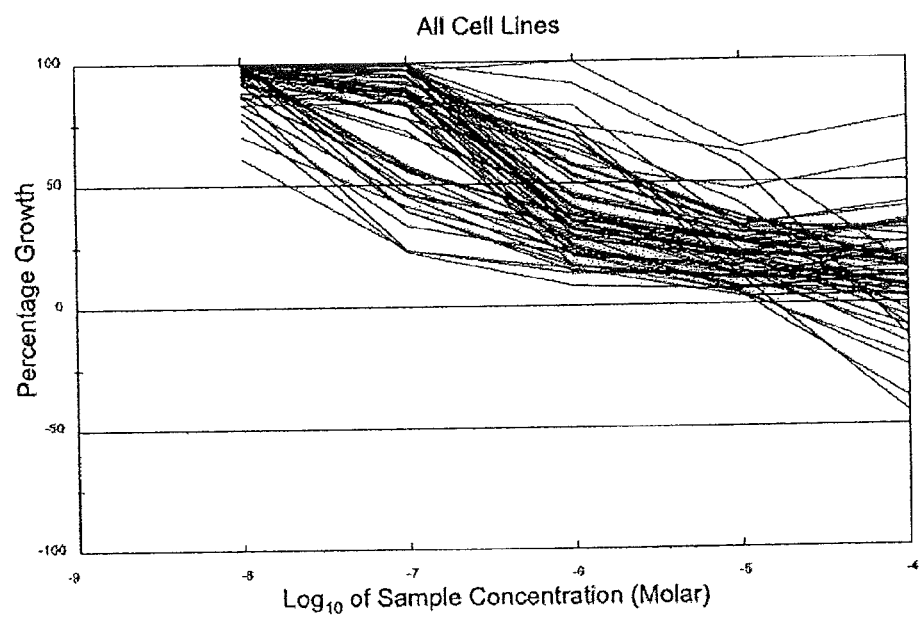
FIG. 4 is a dose-response curve of percentage growth for each of the cell lines shown in Table 4 of the specification.
Figure 5:
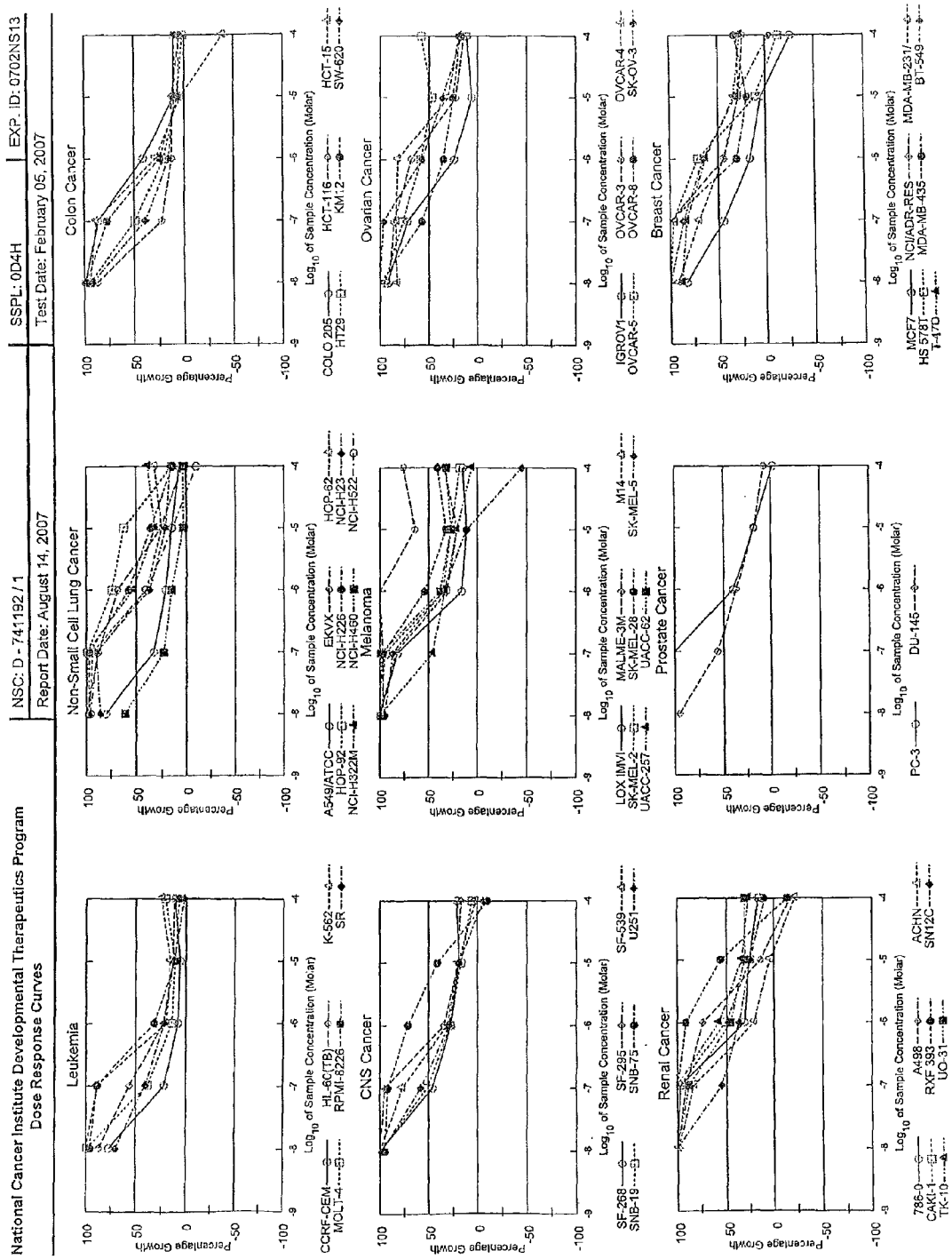
FIG. 5 are dose response curves for each of the cancer types shown in Table 4 of the specification.
Figure 6:
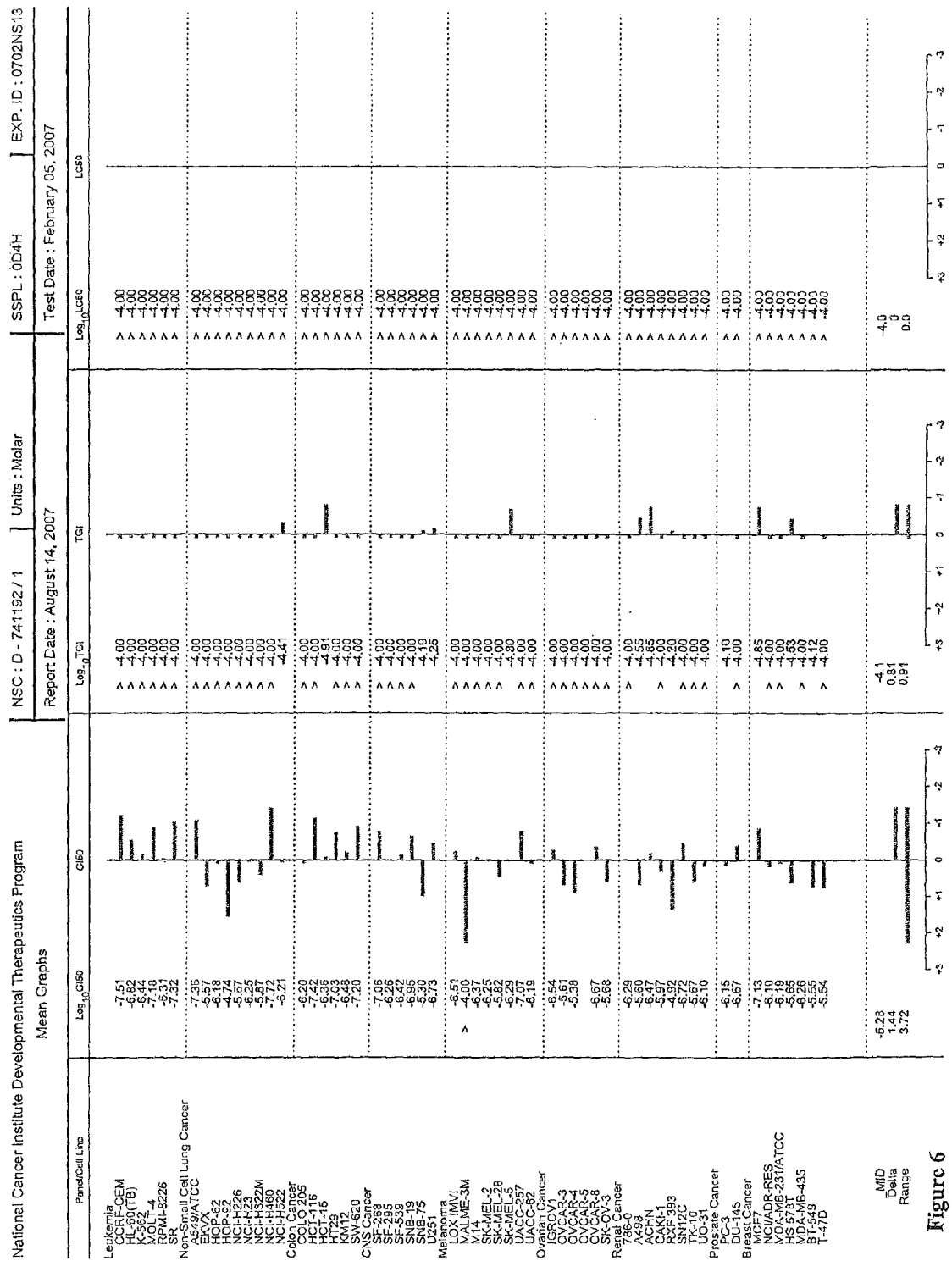
FIG. 6 shows mean graphs for each of the cancer types and corresponding cell lines shown in Table 4 of the specification.

Compound 3 was evaluated in a 60 preclinical in vitro tumor screening panel of the National Cancer Institute and showed excellent cytotoxicity in a wide range of tumors with a $GI_{50}$ from $3.12 \times 10^{-8}$ M to $10^{-6}$ M with $GI_{50}$ against 10 tumors in the $10^{-8}$ M and $GI_{50}$ $10^{-7}$ M against 29 tumor cell lines. Compound 3, when compared in a COMPARE ANALYSIS, also suggested a mechanism of cytotoxicity via inhibition of dihydrofolate reductase and/or dihydroorotate dehydrogenase (Table 4). FIG. 4 is a dose-response curve of percentage growth for each of the cell lines shown in Table 4. FIG. 5 are dose response curves for each of the cancer types shown in Table 4. FIG. 6 shows mean graphs for each of the cancer types and corresponding cells lines shown in Table 4.

TABLE 4

National Cancer Institute Developmental Therapeutics Program
In-Vitro Testing Results NSC: D-741192/1  Experiment ID: 0702NS13  Test Type: 08  Units: Molar
Report Date: May 03, 2007  Test Date: Feb. 05, 2007  ONS:  MC:
COMI: ZY/AG 145-136 (45284)  Stain Reagent: SRB Dual-Pass Related  SSPL: 0D4H Log10 Concentration

| Panel/Cell Line | Time Zero | Ctrl | Mean Optical Densities −8.0 | −7.0 | −6.0 | −5.0 | −4.0 | Percent Growth −8.0 | −7.0 | −6.0 | −5.0 | −4.0 | GI50 | TGI | LC50 |
|---|---|---|---|---|---|---|---|---|---|---|---|---|---|---|---|
| Leukemia | | | | | | | | | | | | | | | |
| OCRF-CEM | 0.390 | 1.286 | 1.083 | 0.587 | 0.462 | 0.446 | 0.485 | 77 | 22 | 8 | 6 | 11 | 3.12E−6 | >1.00E−4 | >1.00E−4 |
| HL-60(TB) | 0.553 | 2.179 | 1.966 | 1.481 | 0.921 | 0.760 | 0.756 | 87 | 56 | 23 | 13 | 12 | 1.50E−7 | >1.00E−4 | >1.00E−4 |
| K-562 | 0.174 | 0.986 | 1.012 | 0.899 | 0.333 | 0.201 | 0.380 | 103 | 89 | 20 | 16 | 26 | 3.56E−7 | >1.00E−4 | >1.00E−4 |
| MOLT-4 | 0.473 | 1.674 | 1.664 | 0.944 | 0.637 | 0.602 | 0.726 | 99 | 39 | 14 | 11 | 21 | 6.61E−8 | >1.00E−4 | >1.00E−4 |
| RPMI-8226 | 0.380 | 0.926 | 0.903 | 0.867 | 0.556 | 0.441 | 0.419 | 96 | 89 | 32 | 11 | 7 | 4.89E−7 | >1.00E−4 | >1.00E−4 |
| SR | 0.421 | 1.274 | 1.020 | 0.768 | 0.611 | 0.525 | 0.440 | 70 | 41 | 22 | 12 | 2 | 4.84E−8 | >1.00E−4 | >1.00E−4 |
| Non-Small Cell Lung Cancer | | | | | | | | | | | | | | | |
| AS45/ATCC | 0.201 | 1.071 | 0.901 | 0.486 | 0.382 | 0.332 | 0.263 | 30 | 33 | 21 | 15 | 7 | 4.34E−8 | >1.00E−4 | >1.00E−4 |
| EKVX | 0.181 | 0.519 | 0.524 | 0.478 | 0.412 | 0.270 | 0.194 | 101 | 68 | 68 | 26 | 4 | 2.71E−8 | >1.00E−4 | >1.00E−4 |
| HOP-52 | 0.518 | 1.498 | 1.467 | 1.435 | 0.911 | 0.751 | 0.829 | 97 | 94 | 40 | 25 | 32 | 6.54E−7 | >1.00E−4 | >1.00E−4 |
| HOP-92 | 0.757 | 1.144 | 1.145 | 1.141 | 1.051 | 1.009 | 0.841 | 100 | 96 | 74 | 62 | 15 | 1.81E−5 | >1.00E−4 | >1.00E−4 |
| NCI-H226 | 0.989 | 2.075 | 2.055 | 2.043 | 1.606 | 1.377 | 1.139 | 98 | 97 | 57 | 36 | 14 | 2.14E−6 | >1.00E−4 | >1.00E−4 |
| NCI-H23 | 0.496 | 1.650 | 1.489 | 1.840 | 0.919 | 0.737 | 0.675 | 86 | 90 | 37 | 21 | 16 | 5.55E−7 | >1.00E−4 | >1.00E−4 |
| NCI-H322M | 0.437 | 1.127 | 1.150 | 1.130 | 0.801 | 0.558 | 0.706 | 103 | 101 | 53 | 32 | 39 | 1.35E−6 | >1.00E−4 | >1.00E−4 |
| NCI-H460 | 0.218 | 2.023 | 1.312 | 0.639 | 0.491 | 0.272 | 0.285 | 61 | 23 | 15 | 3 | 3 | 1.93E−8 | >1.00E−4 | >1.00E−4 |
| NCI-H522 | 0.818 | 1.811 | 1.775 | 1.706 | 1.213 | 0.929 | 0.737 | 96 | 89 | 40 | 14 | −10 | 6.22E−7 | 3.88E−5 | >1.00E−4 |
| Colon Cancer | | | | | | | | | | | | | | | |
| COLO 205 | 0.239 | 0.893 | 0.884 | 0.804 | 0.506 | 0.310 | 0.308 | 99 | 86 | 41 | 11 | 11 | 6.38E−7 | >1.00E−4 | >1.00E−4 |
| HCT-116 | 0.217 | 1.954 | 1.728 | 0.823 | 0.441 | 0.448 | 0.308 | 87 | 23 | 13 | 13 | 6 | 3.81E−8 | >1.00E−4 | >1.00E−4 |
| HCT-15 | 0.242 | 1.070 | 1.023 | 0.967 | 0.479 | 0.273 | 0.148 | 94 | 68 | 29 | 4 | −39 | 4.34E−7 | 1.22E−5 | >1.00E−4 |
| HT29 | 0.206 | 1.369 | 1.303 | 0.773 | 0.445 | 0.287 | 0.226 | 94 | 49 | 21 | 7 | 2 | 9.39E−8 | >1.00E−4 | >1.00E−4 |
| KM12 | 0.448 | 1.635 | 1.610 | 1.365 | 0.740 | 0.536 | 0.502 | 98 | 77 | 25 | 7 | 5 | 3.30E−7 | >1.00E−4 | >1.00E−4 |
| SW-620 | 0.222 | 1.201 | 1.128 | 0.607 | 0.390 | 0.320 | 0.321 | 92 | 39 | 15 | 10 | 10 | 6.30E−8 | >1.00E−4 | >1.00E−4 |
| CNS Cancer | | | | | | | | | | | | | | | |
| SF-258 | 0.374 | 1.402 | 1.439 | 0.850 | 0.547 | 0.573 | 0.592 | 104 | 45 | 27 | 19 | 21 | 8.62E−8 | >1.00E−4 | >1.00E−4 |
| SF-295 | 0.589 | 1.716 | 1.768 | 1.661 | 0.959 | 0.795 | 0.762 | 105 | 95 | 34 | 20 | 17 | 5.47E−7 | >1.00E−4 | >1.00E−4 |
| SF-539 | 0.432 | 1.548 | 1.556 | 1.290 | 0.774 | 0.659 | 0.460 | 101 | 77 | 31 | 20 | 2 | 3.81E−7 | >1.00E−4 | >1.00E−4 |
| SNB-19 | 0.290 | 1.079 | 1.079 | 0.694 | 0.508 | 0.425 | 0.337 | 100 | 51 | 28 | 17 | 6 | 1.13E−7 | >1.00E−4 | >1.00E−4 |
| SNB-75 | 0.615 | 1.216 | 1.187 | 1.169 | 1.039 | 0.863 | 0.555 | 95 | 92 | 71 | 41 | −10 | 5.03E−6 | 6.44E−5 | >1.00E−4 |
| U251 | 0.283 | 1.258 | 1.272 | 0.864 | 0.570 | 0.473 | 0.266 | 98 | 53 | 29 | 19 | −6 | 1.84E−7 | 5.66E−5 | >1.00E−4 |
| Melanoma | | | | | | | | | | | | | | | |
| LOXIMVI | 0.265 | 1.475 | 1.547 | 1.266 | 0.461 | 0.404 | 0.450 | 106 | 52 | 16 | 11 | 15 | 3.08E−7 | >1.00E−4 | >1.00E−4 |
| MALME-3M | 0.534 | 1.015 | 0.997 | 0.999 | 1.043 | 0.844 | 0.901 | 96 | 97 | 106 | 64 | 78 | >1.00E−4 | >1.00E−4 | >1.00E−4 |
| M14 | 0.388 | 1.627 | 1.655 | 1.423 | 0.767 | 0.853 | 0.810 | 102 | 84 | 31 | 21 | 34 | 4.31E−7 | >1.00E−4 | >1.00E−4 |
| SK-MEL-2 | 0.891 | 2.450 | 2.421 | 2.364 | 1.428 | 1.298 | 1.156 | 98 | 95 | 35 | 27 | 18 | 5.58E−7 | >1.00E−4 | >1.00E−4 |
| SK-MEL-23 | 0.578 | 1.603 | 1.650 | 1.574 | 1.130 | 0.910 | 1.002 | 105 | 97 | 54 | 32 | 41 | 1.51E−6 | >1.00E−4 | >1.00E−4 |
| SK-MEL-5 | 0.339 | 1.414 | 1.355 | 1.270 | 0.716 | 0.460 | 0.167 | 95 | 87 | 35 | 11 | −45 | 5.13E−7 | 1.59E−5 | >1.00E−4 |
| UACC-257 | 0.609 | 1.981 | 2.013 | 1.239 | 1.063 | 0.692 | 0.686 | 102 | 46 | 33 | 21 | 8 | 6.45E−8 | >1.00E−4 | >1.00E−4 |
| UACC-62 | 0.698 | 2.085 | 2.074 | 2.063 | 1.230 | 1.075 | 1.139 | 99 | 99 | 38 | 27 | 32 | 6.41E−7 | >1.00E−4 | >1.00E−4 |
| Ovarian Cancer | | | | | | | | | | | | | | | |
| IGROV1 | 0.152 | 0.529 | 0.502 | 0.422 | 0.244 | 0.173 | 0.194 | 93 | 72 | 24 | 6 | 11 | 2.87E−7 | >1.00E−4 | >1.00E−4 |
| OVCAR-3 | 0.329 | 1.222 | 1.145 | 1.093 | 0.936 | 0.525 | 0.457 | 91 | 86 | 66 | 22 | 14 | 2.48E−6 | >1.00E−4 | >1.00E−4 |
| OVCAR-4 | 0.562 | 1.494 | 1.336 | 1.345 | 1.330 | 0.843 | 0.738 | 83 | 84 | 82 | 30 | 19 | 4.16E−6 | >1.00E−4 | >1.00E−4 |
| OVCAR-5 | 0.460 | 0.939 | 0.915 | 0.825 | 0.734 | 0.652 | 0.738 | 96 | 77 | 56 | 47 | 58 | | >1.00E−4 | >1.00E−4 |
| OVCAR-6 | 0.323 | 1.364 | 1.390 | 0.821 | 0.689 | 0.567 | 0.508 | 102 | 57 | 36 | 25 | 18 | 2.16E−7 | >1.00E−4 | >1.00E−4 |
| SK-OV-3 | 0.341 | 1.046 | 1.085 | 1.026 | 0.741 | 0.593 | 0.456 | 106 | 97 | 57 | 36 | 16 | 2.09E−6 | >1.00E−4 | >1.00E−4 |
| Renal Cancer | | | | | | | | | | | | | | | |
| 785-0 | 0.739 | 2.801 | 2.852 | 2.733 | 1.379 | 1.267 | 1.070 | 102 | 97 | 31 | 26 | 16 | 5.14E−7 | >1.00E−4 | >1.00E−4 |
| A498 | 0.248 | 1.550 | 1.556 | 1.496 | 1.391 | 1.033 | 0.766 | 101 | 91 | 74 | 14 | −17 | 2.49E−6 | 2.85E−5 | >1.00E−4 |
| ACHN | 0.459 | 1.484 | 1.472 | 1.311 | 0.676 | 0.495 | 0.359 | 89 | 83 | 21 | 4 | −22 | 3.42E−7 | 1.41E−5 | >1.00E−4 |
| CAKI-1 | 0.258 | 1.038 | 1.078 | 1.014 | 0.670 | 0.472 | 0.397 | 105 | 97 | 51 | 25 | 15 | 1.08E−6 | >1.00E−4 | >1.00E−4 |

TABLE 4-continued

National Cancer Institute Developmental Therapeutics Program
In-Vitro Testing Results NSC: D-741192/1  Experiment ID: 0702NS13  Test Type: 08  Units: Molar
Report Date: May 03, 2007  Test Date: Feb. 05, 2007  ONS:  MC:
COMI: ZY/AG 145-136 (45284)  Stain Reagent: SRB Dual-Pass Related  SSPL: 0D4H Log10 Concentration

| Panel/Cell Line | Time Zero | Ctrl | Mean Optical Densities −8.0 | −7.0 | −6.0 | −5.0 | −4.0 | Percent Growth −8.0 | −7.0 | −6.0 | −5.0 | −4.0 | GI50 | TGI | LC50 |
|---|---|---|---|---|---|---|---|---|---|---|---|---|---|---|---|
| RXF 399 | 0.409 | 0.699 | 0.721 | 0.716 | 0.672 | 0.570 | 0.351 | 108 | 107 | 91 | 56 | −14 | 1.20E−5 | 6.26E−5 | <1.00E−4 |
| SN12C | 0.345 | 1.182 | 1.196 | 0.606 | 0.658 | 0.552 | 0.419 | 102 | 55 | 37 | 25 | 9 | 1.89E−7 | >1.00E−4 | >1.00E−4 |
| TK-10 | 0.455 | 0.954 | 1.038 | 1.052 | 0.762 | 0.635 | 0.595 | 110 | 113 | 58 | 34 | 27 | 2.15E−6 | >1.00E−4 | >1.00E−4 |
| UO-31 | 0.234 | 1.020 | 1.057 | 0.923 | 0.593 | 0.481 | 0.476 | 105 | 88 | 46 | 31 | 31 | 7.90E−7 | >1.00E−4 | >1.00E−4 |
| Prostate Cancer | | | | | | | | | | | | | | | |
| PC-3 | 0.499 | 1.471 | 1.514 | 1.577 | 0.384 | 0.675 | 0.489 | 104 | 111 | 40 | 18 | −2 | 7.18E−7 | 7.95E−5 | >1.00E−4 |
| DU-145 | 0.195 | 0.694 | 0.857 | 0.589 | 0.453 | 0.320 | 0.243 | 95 | 56 | 37 | 18 | 7 | 2.12E−7 | >1.00E−4 | >1.00E−4 |
| Breast Cancer | | | | | | | | | | | | | | | |
| MCF7 | 0.227 | 1.235 | 1.090 | 0.680 | 0.398 | 0.273 | 0.169 | 63 | 45 | 17 | 5 | −26 | 7.34E−8 | 1.41E−5 | >1.00E−4 |
| NCWADR-RES | 0.646 | 1.868 | 1.863 | 1.863 | 1.187 | 0.998 | 0.942 | 100 | 100 | 44 | 29 | 24 | 7.87E−7 | >1.00E−4 | >1.00E−4 |
| MDA-MB-231/ATCC | 0.540 | 1.381 | 1.311 | 1.183 | 0.919 | 0.781 | 0.793 | 92 | 70 | 45 | 29 | 30 | 6.41E−7 | >1.00E−4 | >1.00E−4 |
| HS 576T | 0.718 | 1.226 | 1.248 | 1.212 | 1.077 | 0.774 | 0.628 | 104 | 97 | 71 | 11 | −13 | 2.22E−6 | 2.94E−5 | >1.00E−4 |
| MDA-MB-435 | 0.397 | 1.528 | 1.569 | 1.576 | 0.750 | 0.627 | 0.785 | 104 | 104 | 31 | 20 | 33 | 5.54E−7 | >1.00E−4 | >1.00E−4 |
| BT-549 | 0.318 | 0.810 | 0.623 | 0.740 | 0.638 | 0.475 | 0.304 | 103 | 85 | 65 | 32 | −4 | 2.83E−6 | 7.58E−5 | >1.00E−4 |
| T-47D | 0.387 | 0.901 | 0.839 | 0.615 | 0.713 | 0.684 | 0.524 | 88 | 83 | 63 | 34 | 27 | 2.90E−6 | >1.00E−4 | >1.00E−4 |

Figure 7A:
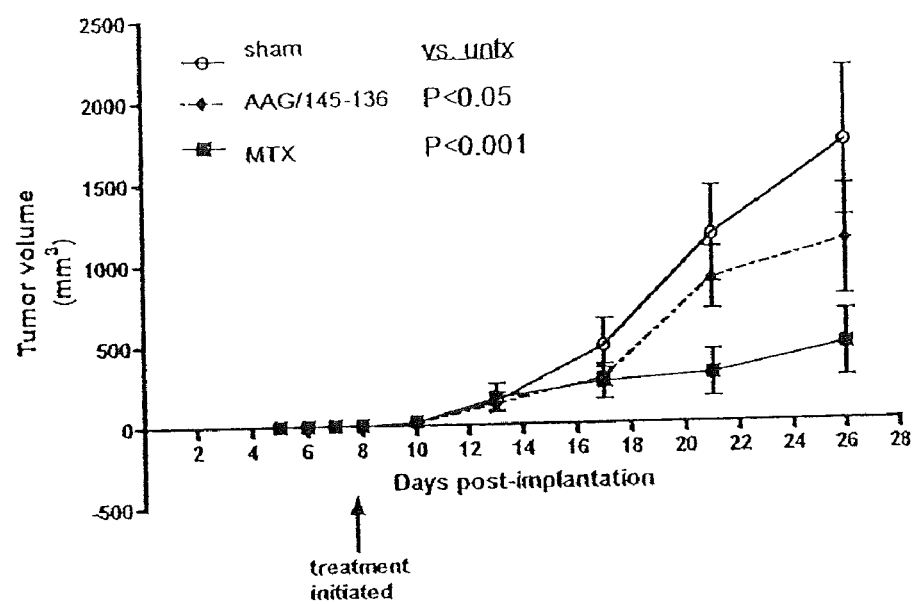
FIGS. 7A, B illustrate tumor parameters of primary B16-F10 tumors in athymic mice in response to drugs given at 25 mg/kg 3× weekly (M, W, F).
Figure 7B:
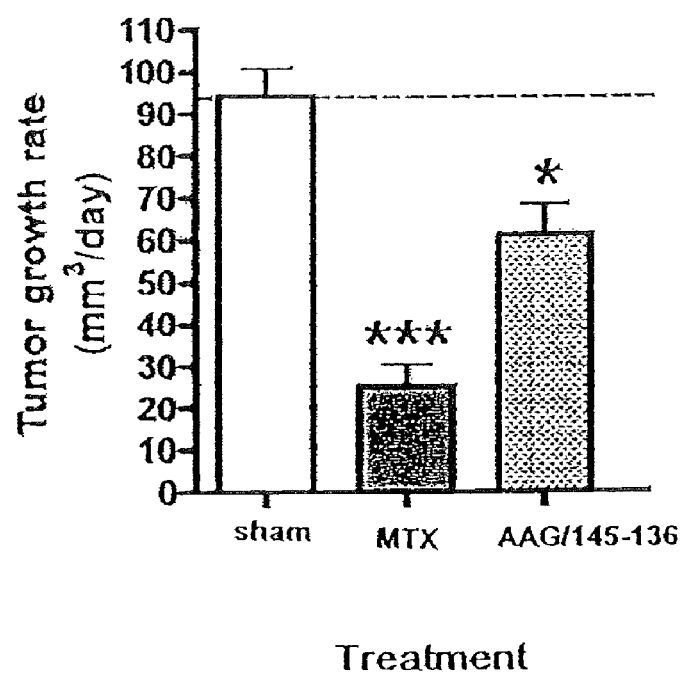
FIG. 7B is a bar graph of tumor growth rate.

Compound 3 underwent evaluation in a B16-F10 tumor model in vivo. The antitumor activity of Compound 3 is shown in FIG. 7. When 25 mg/kg of Compound 3 was administered to athymic mice three times weekly, it demonstrated potent antitumor activity, with respect to tumor volume (FIG. 7A) and tumor growth rate (FIG. 7B) compared to administration of methotrexate and untreated animals (sham).

Figure 8:
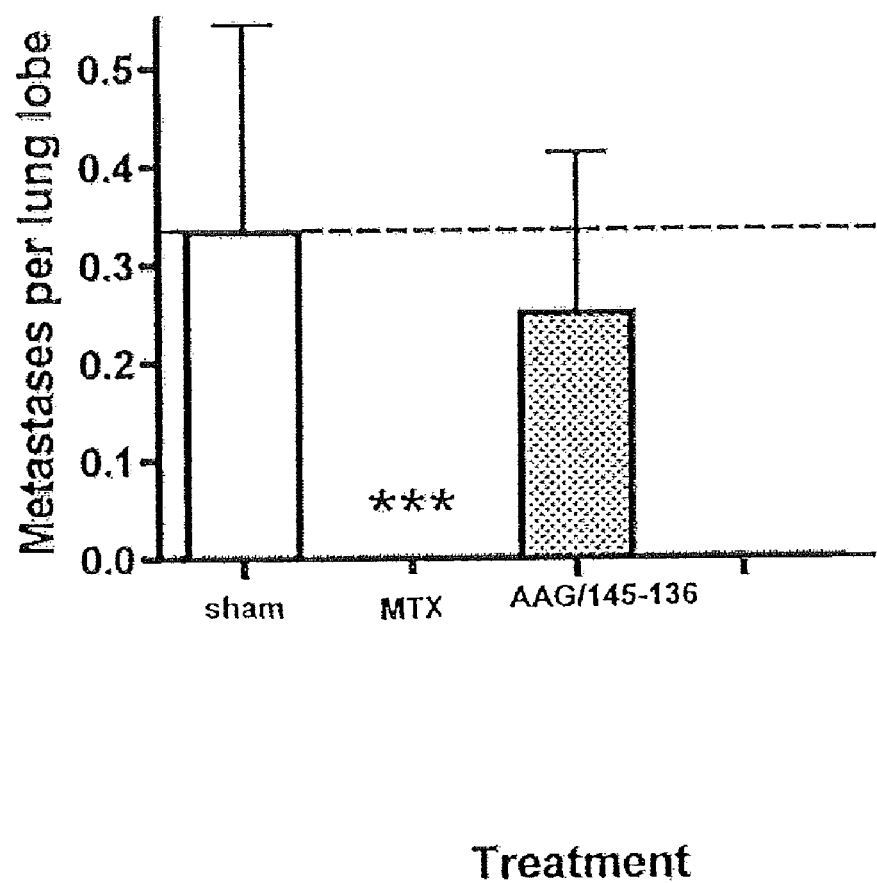
FIG. 8 illustrates metastasis of B16-F10 tumors to the lung in response to drugs given at 25 mg/kg 3× weekly (M, W, F).
Figure 9:
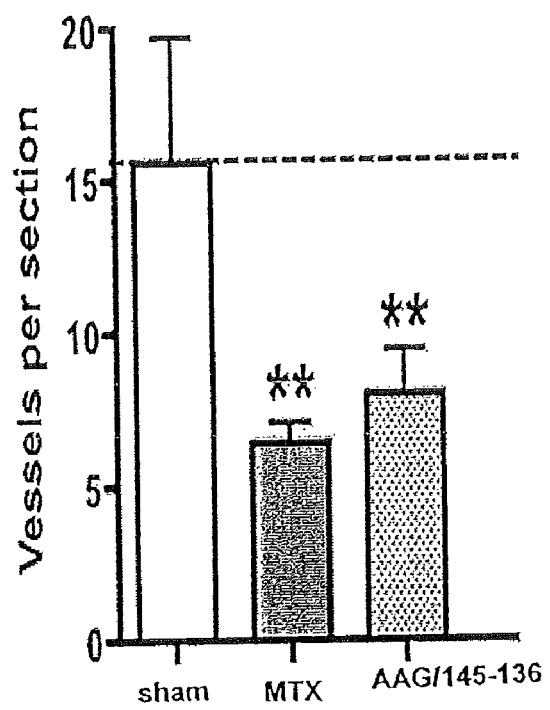
FIG. 9 illustrates vascularity of B16-F10 tumors in athymic mice in response to drugs given at 25 mg/kg 3× weekly (M, W, F).

FIG. 8 shows the decrease in metastasis compared to the sham. FIG. 9 shows the decrease in vascularity of the B16-F10 tumors compared to the sham.

The results demonstrate compounds of structure 3 have antitumor activity in vitro and in vivo along with both cytostatic and cytotoxic activity.

Example 2

Compounds Derived from Compound of Formula II

An example of a compound derived from Compound II is as follows:

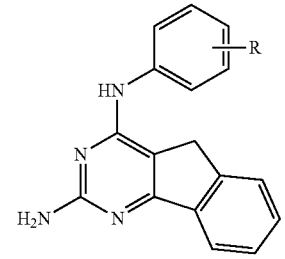

Eight compounds having different substituents for R were synthesized and their activity was assessed in various assays. The compounds, assays and the results of these assays are shown in Table 5. A preferred compound was AAG145-344, in which R=H. This compound had a Flk-1 kinase activity of 5.1, which is lower than the Flk-1 kinase activity of 12.9 found for the standard, SU5416.

TABLE 5

| Compound | EGFR kinase | IRREVERSIBLE EGFR | Flk-1 kinase | Flt-1 kinase | PDGFR-β kinase | A431 cytotoxicity | CAM angiogenesis |
|---|---|---|---|---|---|---|---|
| AAG145-335 R = 3-Cl | 45.1 | | | | | | 3.92 |
| AAG155-336 R = 3-Br | 98.8 | | 167.5 | | | | 20.30 |
| AAG145-340 R = 4-Cl | >300 | | 132.9 | | | | 2.60 |
| AAG145-341 R = 4-Br | >300 | | 163.1 | | | | 4.70 |
| AAG145-342 R = 2-isopropyl | 23 | | 198.5 | | | | |
| AAG145-344 R = H | 232.7 | | 5.1 | | | | |
| AAG145-346 R = 3-F | >300 | | 73.0 | | | | |

TABLE 5-continued
| Compound | EGFR kinase | IRREVERSIBLE EGFR | Flk-1 kinase | Flt-1 kinase | PDGFR-β kinase | A431 cytotoxicity | CAM angiogenesis |
| --- | --- | --- | --- | --- | --- | --- | --- |
| AAG145-347 R = 4-F | >300 | | 21.9 | | | | |
| SU5416 | | | 12.9 | | | | 0.04 |
| PD153035 | 0.23 | | | | | | |
| PD168393 | 0.13 | 0.521 | | | | | |
| cisplatin | | | | | | 10.6 | |
| DMBI | | | | | 3.75 | | |
| VEGF inhibitor | | | | 11.9 | | | |
Example 3
Synthesis of 5-Substituted Thiophenyl Pyrimido[4,5-b]indol-2,4-diamines
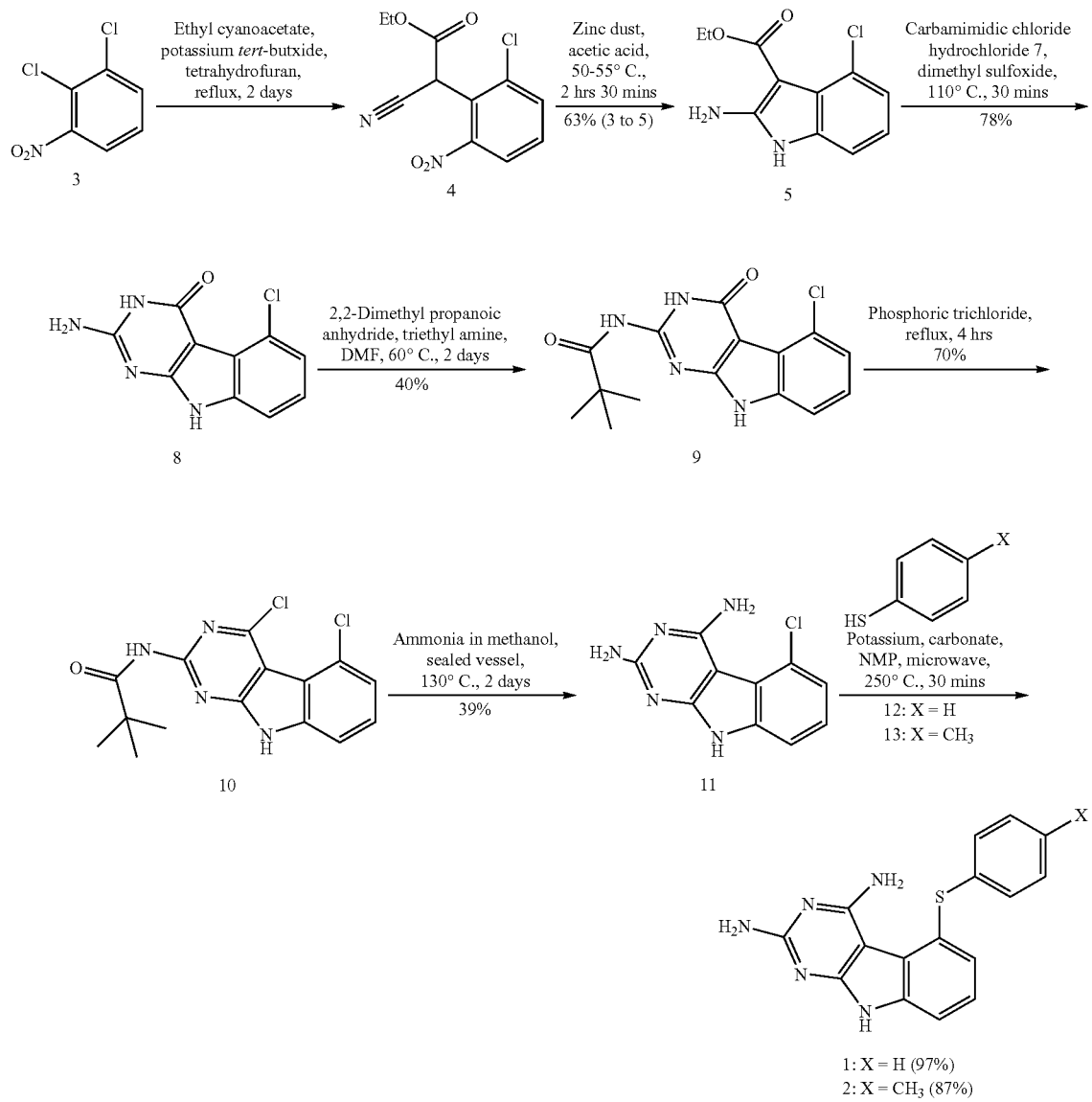

Scheme 2

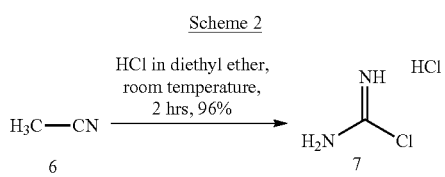

Chemical Discussion

The synthesis of target compounds commenced from commercially available 1,2-dichloro-3-nitro-benzene 3 and ethyl cyanoacetate. Ethyl cyanoacetate was initially treated with base potassium tert-butoxide and 3 was added later to the reaction. Displacement of the chloro group of 3 by the ethyl cyanoacetate anion provided compound 4 as a viscous yellow liquid. Reduction of the nitro group of 4 followed by autocyclization produced compound 5 as a pink solid. Use of fresh or activated zinc powder is recommended for this reaction. Cyclocondensation of 5 with carbamimidic chloride hydrochloride 7 produced the tricyclic compound 8 as a brown solid (synthesis of 7 is provided in Scheme 2). Protection of the 2-amino group of 8 using 2,2-dimethyl propanoic anhydride, under basic conditions, produced 9. Compound 10 was prepared by treating 9 with phosphoric trichloride at reflux. Displacement of the 4-chloro with ammonia, and simultaneous deprotection of the 2-amino group of 10, was achieved using a sealed vessel; thus the 2,4-diamino compound 11 was obtained in 39% yield as a key intermediate. Treatment of 11 with the appropriate substituted benzenethiol provided target compounds 1 and 2, in yields of 97% and 87%, respectively. This reaction was carried out under basic conditions in a microwave (Initiator® from Biotage).

Methods

All evaporations were carried out in vacuo with a rotary evaporator. Analytical samples were dried in vacuo in a Chem Dry drying apparatus over $P_2O_5$. Thin-layer chromatography (TLC) was performed on silica gel plates. Spots were visualized by UV light (254 and 365 nm). Purification by column chromatography was carried out using Merck silica gel 60 (200-400 mesh). The weight of silica gel for column chromatography was in the range of 100-200 times the weight of the crude compound being purified. All columns were wet packed. Solvent systems were reported ratios of solvents. Melting points were determined on a Mel-Temp II melting point apparatus with a digital thermometer and were uncorrected. 1H NMR spectra were recorded on a Bruker WH—300 (300 MHz) NMR spectrometer. The chemical shift (δ) values are reported as parts per million (ppm) relative to tetramethylsilane as internal standard; s=singlet, d=doublet, t=triplet, q=quartet, m=multiplet, bs=broad singlet, exch=protons exchangeable by addition of $D_2O$. Elemental analyses were performed by Atlantic Microlab. Inc., Norcross, Ga. Elemental compositions were ±0.4% of the calculated values. All solvents and chemicals were purchased from Aldrich Chemical Co. and Fisher Scientific and were used as received.

Ethyl(2-chloro-2-nitrophenyl)(cyano)acetate (4)

To an ice cold solution of ethylcyanoacetate (10.9 mL, 102.4 mmol) in anhydrous THF (170 mL) under nitrogen, was added potassium tert-butoxide (12.7 g, 107.5 mmol). The formed white suspension was stirred for 15 minutes, then treated with 2,3-dichloronitrobenzene (9.83 g, 51.2 mmol). The suspension was heated at reflux for 48 hours. The resulting reddish brown solution was poured into water, and the aqueous mixture was acidified to pH 2 with concentrated HCl. The mixture was extracted with ether (3×150 mL) and then the combined organic phase was dried (using $Na_2SO_4$) and concentrated to give a dark oil. Flash chromatography using 10:1 hexane:ethyl acetate in a column packed with silica gel, 10 times the weight of the dark oil, provided a viscous yellow liquid 4, which was used without further purification for the next step. TLC Rf 0.23 (hexane-ethyl acetate 3:1). $^1$H NMR δ 1.33-1.38 (t, 3H, $CH_3$); 4.29-4.35 (q, 2H, $CH_2$); 7.59-8.14 (m, 3H, phenyl).

Ethyl-2-amino-4-chloro-1H-indole-3-carboxylate (5)

4 (18 g, 67 mmol), in 250 mL glacial acetic acid, was treated with a single charge of 18 g of zinc dust. The mixture was heated at 55° C. for 45 minutes. Later, 6 g more zinc dust was added. After heating for another 105 minutes, the yellow mixture was filtered through a pad of celite. The pad was washed with acetic acid and the filtrate was concentrated to a residue that was distributed between chloroform and water. The organic phase was washed with $NaHCO_3$ (5%) to provide a pink precipitate which was filtered, dried over $P_2O_5$, dissolved in methanol, added silica gel and converted to a silica gel plug by removing the solvent under reduced pressure. The plug was transferred on top of a column packed with silica gel, ten times the weight of plug, eluted with hexane, chloroform, 5% ethylacetate in chloroform and 10% ethylacetate in chloroform. Fractions containing the product 5 (TLC) were pooled and evaporated to give a pink solid. The overall yield from 3 to 5 was 63%. TLC Rf 0.187 (hexane-chloroform 1:1); mp 140-142° C.; $^1$H NMR (DMSO-d6) δ 1.25-1.28 (t, 3H, $CH_3$); 4.18-4.20 (q, 2H, $CH_2$); 6.85 (bs, 2H, 2-NH2, exch); 6.92-7.09 (m, 3H, phenyl); 10.93 (bs, 1H, 9-NH, exch). Anal. Calculated ($C_{11}H_{11}ClN_2O_2$): C, 55.36; H, 4.65; N, 11.74; Cl, 14.85. Found: C, 55.39; H, 4.60; N, 11.65; Cl, 14.96.

Carbamimidic Chloride Hydrochloride (7)

Cyanamide (4.2 g, 0.1 mol) was dissolved in 100 mL of diethyl ether in a 500 mL round bottom flask. The mixture was stirred under nitrogen. 100 mL of 2M HCl in diethyl ether was added to the reaction flask via a 250 mL dropping funnel. Stirring was continued for 2 hours at room temperature. The white salt which precipitated out was filtered and dried. The overall yield for 7 was 96%. 7 was used for the next step without further purification.

2-Amino-5-chloro-3,9-dihydro-4H-pyrimido[4,5-b]indol-4-one (8)

1 g methyl sulfone was heated to melting. 7 (106.22 mg, 1.37 mmol) was added and the resulting mixture was stirred and heated at 110-120° C. to dissolve completely. 5 (200 mg, 0.837 mmol) was added in one part to the reaction mixture. Stirring was continued for 30 minutes. About 10 mL water was added to quench the reaction. Ammonia water was added to neutralize the reaction mixture. Solid precipitated out. This solid was filtered. Obtained solid was dissolved in chloroform and methanol, dried (using $Na_2SO_4$) and recrystallized. The overall yield was 78%. TLC Rf 0.33 (chloroform-methanol 1:1); mp>250° C.; $^1$H NMR (DMSO-d6) δ 6.57 (bs, 2H, 2-$NH_2$, exch); 7.04-7.17 (m, 3H, phenyl); 10.41 (s, 11-1, 9-NH, exch); 11.64 (s, 1H, 3-NH, exch). Anal. Calculated ($C_{10}H_7ClN_4O$. $0.3CH_3OH$): C, 50.65; H, 3.38; N, 22.94; Cl, 14.52. Found: C, 50.91; H, 3.34; N, 22.60; Cl, 14.77.

N-(5-chloro-4-oxo-4,9-dihydro-3H-pyrimido[4,5-b]indol-2-yl)-2,2-dimethyl propanamide (9)

Compound 8 (300 mg, 1.27 mmol), 2-dimethyl propanoic anhydride (713.32 mg, 3.83 mmol), dimethyl aminopyridine (7 mg, 0.06 mmol), triethylamine (514.05 mg, 5.08 mmol) were weighed together in a 50 mL round bottom flask. This flask was placed in an oil bath at 60° C. with stirring for 2 days. Then, to the reaction mixture was added 1 g silica gel. The DMF was removed using oil pump and a silica gel plug was made. The plug was transferred on top of a column packed with silica gel, twenty times the weight of plug, eluted with chloroform, 1% methanol in chloroform and 5% methanol in chloroform. Fractions containing the product 9 (TLC) were pooled and evaporated to give solid compound. The overall yield was 40%. TLC Rf 0.45 (chloroform-methanol 10:1), m.p. 185.8-190.1° C., $^1$H NMR: δ 1.27 (s, 9H, pivaloyl); 7.19-7.40 (m, 3H, phenyl); 11.15 (s, 1H, 9-NH, exch); 11.94 (s, 1H, 9-NH, exch); 12.12 (s, 1H, 3-NH, exch).

N-(4,5-dichloro-9H-pyrimido[4,5-b]indol-2-yl)-2,2-dimethyl propanamide (10)

To 9 (2 g, 6.274 mmol) was added 30 mL of POCl$_3$ in a 250 mL round bottom flask. The reaction mixture was refluxed at 110-120° C. for 4 hours. After this the POCl$_3$ was evaporated and the mixture was neutralized using NH$_4$OH. The aqueous mixture was filtered (the precipitate being the compound). The filtrate also contained some compound. Therefore, it was extracted using chloroform and ethyl acetate. The precipitate obtained was dissolved in chloroform and methanol. Both the dissolved precipitate and extracted filtrate were dried using sodium sulfate overnight. To the solution was added silica, and solvent was removed under reduced pressure to provide a silica gel plug. The plug was transferred on top of a column packed with silica gel, twenty times the weight of plug, eluted with chloroform, 1% methanol in chloroform and 5% methanol in chloroform. Fractions containing the product 10 (TLC) were pooled and evaporated to give a solid. The overall yield was 70%. TLC Rf 0.86 (chloroform-methanol 5:1), m.p. 245.6-246.1° C., $^1$H NMR: δ 1.24 (s, 9H, pivaloyl); 7.37-7.63 (m, 3H, phenyl); 10.32 (s, 1H, 9-NH, exch); 12.96 (s, 1H, 2-NH, exch).

5-Chloro-9H-pyrimido[4,5-b]indole-2,4 diamine propanamide (11)

5 mL methanol was saturated with ammonia in the plastic container (of the sealed tube reaction apparatus), which was cooled in dry ice and acetone. 10 (200 mg, 0.6 mmol) was added to this methanol saturated with ammonia. The solution was stirred at 130° C. for 2 days. Silica gel was added to the reaction mixture and methanol was removed under reduced pressure to make a plug. The plug was transferred on top of a column packed with silica gel, ten times the weight of plug, eluted with chloroform and 1% methanol in chloroform. Fractions containing the product 10 (TLC) were pooled and evaporated to give a solid. The overall yield was 39%. TLC Rf 0.43 (chloroform-methanol 5:1), m.p. 245.2-246.3° C., $^1$H NMR: δ 6.15 (bs, 2H, 4-NH$_2$, exch); 6.85 (bs, 2H, 2-NH$_2$, exch), 7.03-7.24 (m, 3H, phenyl); 11.54 (bs, 1H, 9-NH, exch). Anal. Calculated (C$_{10}$H$_8$ClN$_5$): C, 51.40; H, 3.38; N, 29.97; Cl, 15.17. Found: C, 51.58; H, 3.46; N, 29.86; Cl, 15.05.

General procedure for the synthesis of 5-(substituted-phenylthio)-9H-pyrimido[4,5-b]indole-2,4-diamines 1 and 2

Compound 11 (50 mg, 0.2 mmol), the appropriate thiol (0.9 mmol), and potassium carbonate (120 mg, 0.9 mmol) were added to a 2-5 mL capacity microwave vial. 3 mL NMP was added as solvent and the tube was sealed. The reaction was run in a microwave for 30 minutes at 250° C. After being cooled to room temperature, the reaction mixture was transferred on top of a 3 cm diameter column packed with approximately 40 cm silica gel and eluted with chloroform, 1% methanol in chloroform, 3% methanol in chloroform and 4% methanol in chloroform. Fractions containing the product (TLC) were pooled and evaporated to afford the product 1 and 2.

5-(phenylthio)-9H-pyrimido[4,5-b]indole-2,4-diamine (1)

Using the general procedure described above, compound 1 was obtained by the reaction of 11 with benzene thiol to afford an off-white solid in 97% yield. TLC Rf 0.23 (chloroform-methanol 10:1), m.p.>250° C., $^1$H NMR: δ 6.03 (bs, 2H, 4-NH$_2$, exch); 7.01-7.41 (m, 10H, Ar—H×8, 2-NH$_2$); 11.48 (bs, 1H, 9-NH, exch). Anal. Calculated (C$_{16}$H$_{13}$N$_5$S): C, 62.52; H, 4.26; N, 22.78; S, 10.43. Found: C, 62.51; H, 4.51; N, 22.44; S, 10.35.

5-[(4-methylphenyl)thio]-9H-pyrimido[4,5-b]indole-2,4-diamine (2)

Using the general procedure described above, compound 2 was obtained by the reaction of 11 with 4-methylbenzene thiol to afford an off-white solid in 87% yield. TLC Rf 0.54 (chloroform-methanol 5:1), m.p.>250° C., $^1$H NMR: δ 2.19 (s, 3H, CH$_3$), 6.02 (bs, 2H, 4-NH$_2$, exch); 7.19 (bs, 2H, 2-NH$_2$, exch), 6.97-7.36 (m, 7H, Ar—H×7); 11.46 (bs, 1H, 9-NH, exch). Anal. Calculated (C$_{17}$H$_{15}$N$_5$S): C, 63.53; H, 4.70; N, 21.70; S, 9.98. Found: C, 62.39; H, 4.56; N, 21.00; S, 9.56.

Scheme 3:

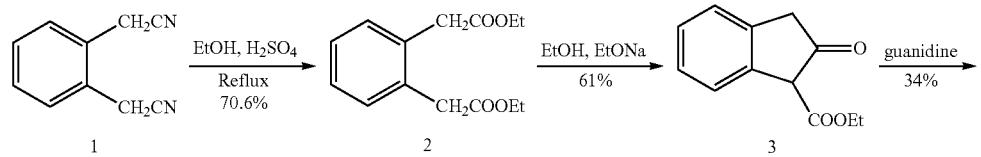

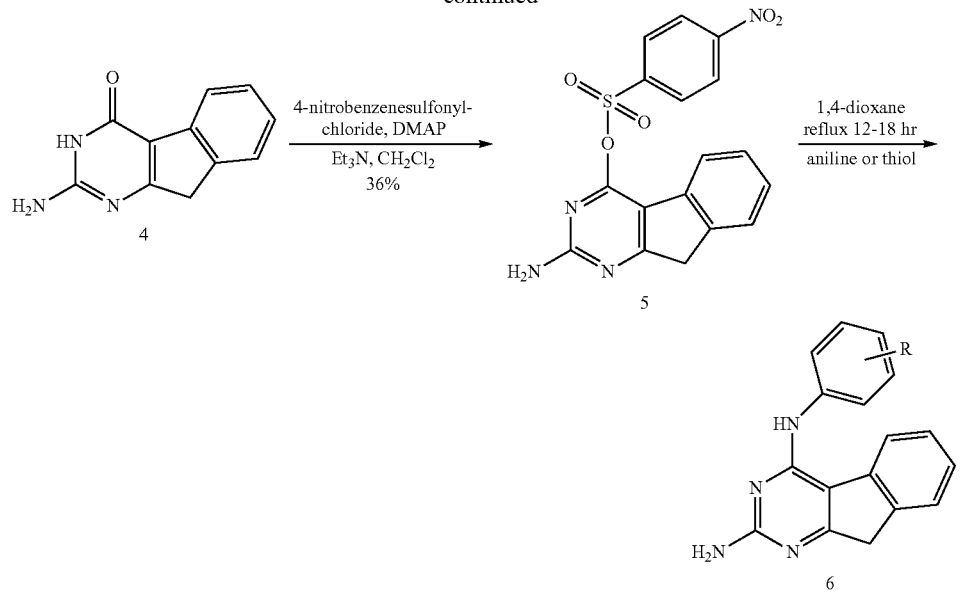

R =
7  2-isopropyl  18%
8  4-isopropyl  59%
9  3-F          18%
10 3-Cl         35%
11 3-Br         50%
12 4-F          31%
13 4-Cl         36%
14 4-Br         61%
15 4-CF$_3$     27%
16 3-CH$_3$O    45%
17 H            37%
18 4-F, 3-Cl    50%
19 2-F, 4-Cl    18%

Chemical Discussion

The synthesis route used to prepare analogues is described in Scheme 3. (2-ethoxycarbonylmethyl-phenyl)-acetic acid ethyl ester 2 (71%) was obtained by hydrolysis of 1,2-phenylenediacetonitrile 1 with concentrated H$_2$SO$_4$. Compound 2 with sodium ethoxide in ethanol gave compound 3 (61%), which further reacted with guanidine in the presence of potassium t-butoxide under 150° C. in a microwave reaction to give compound 4 (34%). To access target compounds, first, compound 4 was tried to turn the 4-oxo to 4-chloro, which traditionally is adopted in synthesizing 4-anilino substituted analogues. However, because of the lower aromaticity of the ring, the chlorination did not run well under known reaction conditions. Compound 4 was decomposed when refluxed with POCl$_3$. Thus, the 4-oxo was converted to 4-sulfonate, which is a good leaving group for SNi reaction. Compound 5 was obtained when treating compound 4 with the 4-nitrobenzensulfonyl chloride (36%). The target compound 6 with different substitution on the phenyl ring was obtained when refluxing compound 5 with corresponding aniline for 12-18 h.

Methods (2-Ethoxycarbonylmethyl-phenyl)-acetic acid ethyl ester (2)

1,2-phenylenediacetonitrile (1.0 g, 6.40 mmol) was dissolved in 5 ml ethyl alcohol and 2 ml concentrated sulfuric acid in a 25 ml round bottom flask. The mixture was stirred and heated to reflux for 6 hours. After neutralizing the reaction solution with ammonium hydroxide, the result solution was extracted with ethyl acetate (3×50 ml). The organic phase was combined and dried with Na$_2$SO$_4$. Concentration of the ethyl acetate afforded a yellow liquid. Running column with hexane: acetyl acetate=10:1, got yellow liquid 1.13 g (70.6%). $^1$H NMR (DMSO-d6): δ 1.24 (t, 6H, CH$_3$), δ 3.7 (s, 4H, CH$_2$CO), δ 4.16 (q, 4H, OCH$_2$), δ 7.3 (d, 4H, Ar—H).

2-oxo-indan-1-carboxylic acid ethyl (3)

Compound 2 (5.6 g, 2 mmol) was diluted in 30 ml ethyl alcohol, and 1.6 g (2.2 mmol) sodium ethoxide was slowly added in a 150 ml round bottom flask, stirring at room temperature for 4 hours to form a yellow clear solution. After neutralizing the reaction solution with dilute hydrochloric acid, the result solution was extracted with ethyl acetate (3×50 ml). The organic phase was combined and dried with Na$_2$SO$_4$. Concentration of the ethyl acetate afforded a brown solid. Running column with hexane: acetyl acetate=10:1, got 2.80 g (61%) white solid. M.p: 59~61° C. $^1$H NMR (DMSO-d6): δ 3.64 (s, 2H, Ar—CH$_2$CO), δ 4.43 (q, 2H, OCH$_2$), δ 7.6 (m, 4H, Ar—H), δ 11.0 (s, 1H, OH, exch).

2-amino-3,9-dihydro-indeno[2,1-d]pyrimidin-4-one (4)

Compound 3 (0.1 g, 0.49 mmol), guanidine hydrochloride (0.05 g, 0.52 mmol) and potassium t-butoxide (0.12 g, 1.1 mmol) were dissolved in 5 ml t-butanol. The condition of microwave reaction is 140° C., 3 hours. The solid was filtered out and washed with methanol. The filtrate was combined and plugs were made with silica gel. Running column with chloroform:methanol=10:1 afforded light yellow solid 23 mg (34%). Mp: ~330° C. (dec.). $^1$H NMR (DMSO-d6): δ 3.65 (s, 2H, CH$_2$), δ 6.71 (s, 2H, NH$_2$, exch), δ 7.0~7.67 (m, 4H, Ar—H), δ 10.93 (s, 1H, NH, exch). CHN Anal. (C$_{11}$H$_9$N$_3$O.0.1H$_2$O): C, H, N.

4-Nitro-benesulfonic acid 2-amino-9H-indeno[2,1-d]pyrimidin-4-ylester (5)

A solution of 4 (0.3 g, 1.5 mmol), triethylamine (0.42 ml, 3 mmol), DMAP (20 mg) and 4-nitrobenzenesulfonyl chloride (0.67 g, 3 mmol) in dichloromethane 40 ml was stirred at room temperature for 4 hours. To the reaction solution was added 1.5 g silica gels to make plugs directly. The column was eluted with Hexane: Chloroform (2:1). Fractions containing the product were pooled and evaporated to afford pure compound 10 as yellow solid 0.21 g (36%). TLC Rf 0.47 (CHCl$_3$/CH$_3$OH, 10:1). Mp: 189.6° C. (dec); $^1$H NMR (DMSO-d6): δ 3.92 (s, 2H, CH$_2$), δ 7.18 (br, 2H, NH$_2$, exch), δ 7.15-7.6 (m, 4H, Ph-H), δ 8.4-8.6 (m, 4H, 4-NO$_2$-Ph-H). HRMS (EI): calculation for C$_{17}$H$_{13}$N$_4$O$_5$S 385.0607. found, 385.0584.

General Procedure for the Synthesis of Compounds 7-19

A 50 ml round-bottom flask was charged with compound 5, substituted thiophenol or aniline (molar ration 1:2) and anhydrous 1,4-dioxane 10 ml. The mixture was heated and kept refluxing for 12-18 hours. Plugs were made directly after stopping the reaction. The column was eluted with hexane/chloroform (2:1). Fractions containing the product were pooled and evaporated to afford pure compound.

N$^4$-(2-Isopropyl-phenyl)-9H-indeno[2,1-d]pyrimidine-2,4-diamine (7)

Compound was synthesized from 4-nitro-benesulfonic acid 2-amino-9H-indeno[2,1-d]pyrimidin-4-ylester 5 (0.1 g, 0.26 mmol) using the general procedure described above to afford 15 mg (18%) as a light brown solid. TLC Rf 0.43 (Et$_3$N/EtOAc/Hex, 1:3:5). Mp: 193.4~195.3° C.; $^1$H NMR (DMSO-d6): δ 1.14-1.16 (d, 6H, 2CH$_3$), δ 3.10-3.24 (m, H, CH), δ 3.70 (s, 2H, CH$_2$), δ 6.13 (br, 2H, NH$_2$, exch), δ 7.11-7.93 (m, 8H, Ph-H), δ 7.91 (s, H, NH, exch). HRMS (EI): calculation for C$_{20}$H$_{21}$N$_4$, 317.1766. found, 317.1751.

N$^4$-(4-Isopropyl-phenyl)-9H-indeno[2,1-d]pyrimidine-2,4-diamine (8)

Compound was synthesized from 4-nitro-benesulfonic acid 2-amino-9H-indeno[2,1-d]pyrimidin-4-ylester 5 (75 mg, 0.76 mmol) using the general procedure described above to afford 36.4 mg (59%) as a light brown solid. TLC Rf 0.30 (CHCl$_3$/CH$_3$OH, 10:1). Mp: 178.5~180.4° C.; $^1$H NMR (DMSO-d6): δ 3.76 (s, 2H, CH$_2$), δ 6.5 (br, 2H, NH$_2$, exch), δ 7.14-7.92 (m, 8H, Ph-H), δ 8.33 (s, H, NH, exch). HRMS (EI): calculation for C$_{20}$H$_{20}$N$_4$, 316.1688. found, 316.1704.

N$^4$-(3-Fluoro-phenyl)-9H-indeno[2,1-d]pyrimidine-2,4-diamine (9)

Compound was synthesized from 4-nitro-benesulfonic acid 2-amino-9H-indeno[2,1-d]pyrimidin-4-ylester 5 (0.15 g, 0.39 mmol) using the general procedure described above to afford 15 mg (13%) as a light brown solid. TLC Rf 0.42 (CHCl$_3$/CH$_3$OH, 10:1). Mp: 198.7~200.1° C.; $^1$H NMR (DMSO-d6): δ 3.8 (s, 2H, CH$_2$), δ 6.6 (br, 2H, NH$_2$, exch), δ 7.1-7.9 (m, 8H, Ph-H), δ 8.4 (s, H, NH, exch). HRMS (EI): calculation for C$_{17}$H$_{13}$FN$_4$, 292.1124. found, 292.1123.

N$^4$-(3-Chloro-phenyl)-9H-indeno[2,1-d]pyrimidine-2,4-diamine (10)

Compound was synthesized from 4-nitro-benesulfonic acid 2-amino-9H-indeno[2,1-d]pyrimidin-4-ylester 5 (0.1 g, 0.26 mmol) using the general procedure described above to afford 22.8 mg (35%) as a light brown solid. TLC Rf 0.65 (CHCl$_3$/CH$_3$OH, 10:1). Mp: 224.1~225.2° C.; $^1$H NMR (DMSO-d6): δ 3.7 (s, 2H, CH$_2$), δ 6.5 (br, 2H, NH$_2$, exch), δ 7.0-7.8 (m, 8H, Ph-H), δ 8.3 (s, H, NH, exch). HRMS (EI): calculation for C$_{17}$H$_{13}$ClN$_4$, 308.0829. found, 308.0838.

N$^4$-(3-Bromo-phenyl)-9H-indeno[2,1-d]pyrimidine-2,4-diamine (11)

Compound was synthesized from 4-nitro-benesulfonic acid 2-amino-9H-indeno[2,1-d]pyrimidin-4-ylester 5 (0.1 g, 0.26 mmol) using the general procedure described above to afford 46 mg (50%) as a light brown solid. TLC Rf 0.47 (Et$_3$N/EtOAc/Hex, 1:3:5). Mp: 233-236° C.; $^1$H NMR (DMSO-d6): δ 3.76 (s, 2H, CH$_2$), δ 6.5 (br, 2H, NH$_2$, exch), δ 7.14-7.92 (m, 8H, Ph-H), δ 8.33 (s, H, NH, exch). HRMS (EI): calculation for C$_{17}$H$_{14}$BrN$_4$, 353.0402. found, 353.0387.

N$^4$-(4-Fluoro-phenyl)-9H-indeno[2,1-d]pyrimidine-2,4-diamine (12)

Compound was synthesized from 4-nitro-benesulfonic acid 2-amino-9H-indeno[2,1-d]pyrimidin-4-ylester 5 (0.12 g, 0.31 mmol) using the general procedure described above to afford 46 mg (50%) as a light brown solid. TLC Rf 0.54 (CHCl$_3$/CH$_3$OH, 10:1). Mp: 204.7~205.8° C.; $^1$H NMR (DMSO-d6): δ 3.72 (s, 2H, CH$_2$), δ 6.38 (br, 2H, NH$_2$, exch), δ 7.11-7.89 (m, 8H, Ph-H), δ 8.19 (s, H, NH, exch). CHN Anal (C$_{17}$H$_{13}$FN$_4$. 0.4H$_2$O): C, H, N, F.

N$^4$-(4-Chloro-phenyl)-9H-indeno[2,1-d]pyrimidine-2,4-diamine (13)

Compound was synthesized from 4-nitro-benesulfonic acid 2-amino-9H-indeno[2,1-d]pyrimidin-4-ylester 5 (0.10 g, 0.26 mmol) using the general procedure described above to afford 30 mg (38%) as a light brown solid. TLC Rf 0.33 (CHCl$_3$/CH$_3$OH, 10:1). Mp: 215.9-216.8° C.; $^1$H NMR (DMSO-d6): δ 1.16-1.22 (d, 6H, 2CH$_3$), δ 2.6-2.9 (m, H, CH), δ 3.7 (s, 2H, CH$_2$), δ 6.3 (br, 2H, NH$_2$, exch), δ 7.2-7.8 (m, 8H, Ph-H), δ 8.1 (s, H, NH, exch). CHN Anal (C$_{17}$H$_{13}$ClN$_4$): C, H, N, Cl.

N$^4$-(4-Bromo-phenyl)-9H-indeno[2,1-d]pyrimidine-2,4-diamine (14)

Compound was synthesized from 4-nitro-benesulfonic acid 2-amino-9H-indeno[2,1-d]pyrimidin-4-ylester 5 (0.13 g, 0.34 mmol) using the general procedure described above to afford 72 mg (61%) as a white-off solid. TLC Rf 0.44 (CHCl$_3$/CH$_3$OH, 10:1). Mp: 213.6~214.8° C.; $^1$H NMR (DMSO-d6): δ 3.75 (s, 2H, CH$_2$), δ 6.45 (br, 2H, NH$_2$, exch), δ 7.14-7.89

(m, 8H, Ph-H), δ 8.31 (s, H, NH, exch). CHN Anal (C₁₇H₁₃BrN₄. 0.6CH₃OH): C, H, N, Br.

N⁴-(4-Trifluoromethyl-phenyl)-9H-indeno[2,1-d]pyrimidine-2,4-diamine (15)

Compound was synthesized from 4-nitro-benesulfonic acid 2-amino-9H-indeno[2,1-d]pyrimidin-4-ylester 5 (0.22 g, 0.57 mmol) using the general procedure described above to afford 44 mg (27%) as a light brown solid. TLC Rf 0.48 (CHC₁₃/CH₃OH, 10:1). Mp: 229.2~230.8° C.; NMR (DMSO-d6): δ 3.8 (s, 2H, CH₂), δ 6.6 (br, 2H, NH₂, exch), δ 7.2-8.0 (m, 8H, Ph-H), δ 8.7 (s, H, NH, exch). CHN Anal (C₁₈H₁₃F₃N₄): C, H, N, F.

N⁴-(3-Methoxyl-phenyl)-9H-indeno[2,1-d]pyrimidine-2,4-diamine (16)

Compound was synthesized from 4-nitro-benesulfonic acid 2-amino-9H-indeno[2,1-d]pyrimidin-4-ylester 5 (75 mg, 0.76 mmol) using the general procedure described above to afford 26.6 mg (45%) as a light brown solid. TLC Rf 0.47 (CHCl₃/CH₃OH, 10:1). Mp: 186.6~187.4° C.; ¹H NMR (DMSO-d6): δ 3.7 (s, 2H, CH₂), δ 3.8 (s, 3H, CH₃), δ 6.4 (br, 2H, NH₂, exch), δ 6.6-7.8 (m, 8H, Ph-H), δ 8.1 (s, H, NH, exch). HRMS (EI): calculation. for C₁₈H₁₆N₄O, 304.1324. found, 304.1390.

N⁴-Phenyl-91'-indeno[2,1-d]pyrimidine-2,4-diamine (17)

Compound was synthesized from 4-nitro-benesulfonic acid 2-amino-9H-indeno[2,1-d]pyrimidin-4-ylester 5 (0.05 g, 0.13 mmol) using the general procedure described above to afford 13.8 mg (37%) as a light brown solid. TLC Rf 0.37 (CHC₁₃/CH₃OH, 10:1). Mp: 215.3~216.9° C.; ¹H NMR (DMSO-d6): δ 3.7 (s, 2H, CH₂), δ 6.4 (br, 2H, NH₂, exch), δ 7.0-7.9 (m, 8H, Ph-H), δ 8.2 (s, H, NH, exch). HRMS (EI): calculation. for C₁₇H₁₄N₄, 274.1218. found, 274.1218.

N⁴-(4-Fluoro-3-chloro-phenyl)-9H-indeno[2,1-d]pyrimidine-2,4-diamine (18)

Compound was synthesized from 4-nitro-benesulfonic acid 2-amino-9H-indeno[2,1-d]pyrimidin-4-ylester 5 (0.1 g, 0.26 mmol) using the general procedure described above to afford 53 mg (52%) as a light brown solid. TLC Rf 0.43 (CHCl₃/CH₃OH, 10:1). Mp: 231.7~232.8° C.; ¹H NMR (DMSO-d6): δ 3.7 (s, 2H, CH₂), δ 6.5 (br, 2H, NH₂, exch), δ 7.1-8.0 (m, 8H, Ph-H), δ 8.3 (s, H, NH, exch). HRMS (EI): calculation for C₁₇H₁₂ClFN₄, 326.0735. found, 326.0744.

N⁴-(2-Fluoro-4-chloro-phenyl)-9H-indeno[2,1-d]pyrimidine-2,4-diamine (19)

Compound was synthesized from 4-nitro-benesulfonic acid 2-amino-9H-indeno[2,1-d]pyrimidin-4-ylester 5 (50 mg, 0.59 mmol) using the general procedure described above to afford 15 mg (18%) as a light brown solid. TLC Rf 0.58 (Et₃N/EtOAc/Hex, 1:3:5). Mp: 234.7~235.7° C.; ¹H NMR (DMSO-d6): δ 3.98 (s, 2H, CH₂), δ 6.37 (br, 2H, NH₂, exch), δ 7.15-7.86 (m, 7H, Ph-H), δ 8.16 (s, H, NH, exch). CHN Anal. (C₁₇H₁₂ClFN₄): C, H, N, Cl, F.

Elemental analysis for Compounds 4, 12-15 and 19 is shown in FIG. 10.

High-resolution mass spectra are shown in Table 6.

TABLE 6

| High-Resolution mass spectra (HRMS) (EI) | | | |
|---|---|---|---|
| # | Formula | Calcd mass | Found mass |
| 5 | C₁₇H₁₃N₄O₅S | 385.0607 | 385.0584 |
| 7 | C₂₀H₂₁N₄ | 317.1766 | 317.1751 |
| 8 | C₂₀H₂₀N₄ | 316.1688 | 316.1704 |
| 9 | C₁₇H₁₃FN₄ | 292.1124 | 292.1123 |
| 10 | C₁₇H₁₃ClN₄ | 308.0829 | 308.0838 |
| 11 | C₁₇H₁₄BrN₄ | 353.0402 | 353.0387 |
| 16 | C₁₈H₁₆N₄O | 304.1324 | 304.1390 |
| 17 | C₁₇H₁₄N₄ | 274.1218 | 274.1218 |
| 18 | C₁₇H₁₂ClFN₄ | 326.0735 | 326.0744 |

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method of inhibiting receptor tyrosine kinase(s), dihydrofolate reductase, thymidylate synthase and/or dihydroorotate dehydrogenase activity in an animal or human in need thereof, comprising administering to said animal or human a therapeutically effective amount in unit dosage form of a compound of formula I:

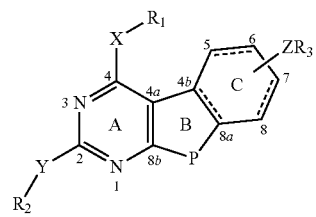

wherein both B and C rings may be completely or partially saturated or unsaturated with respect to bond 4b-8a, 5-6 and 7-8;
X and/or Y=N, NH, O, S, CH₂; P=CR₄R₅ wherein R₄ and R₅=lower alkyl, alkene, alkyne, and all of R₁ and R₂;
R₁=an alkyl having C₂ to C₆, a cycloalkyl having 6 or less carbons, alkene, alkyne, aryl, heteroaryl, substituted aryl, substituted heteroaryl, alkylaryl, alkylheteroaryl, substituted alkylaryl or alkylheteroaryl, and R₁ may be H when said C ring is partially or completely saturated or partially unsaturated; and R₂=H, an alkyl, a cycloalkyl having 6 or less carbons, alkene, alkyne, aryl, heteroaryl, substituted aryl, substituted heteroaryl, alkylaryl, alkylheteroaryl, substituted alkylaryl or alkylheteroaryl;
Z=S, O, NR₆, S—CH₂, CH₂—S, O—CHR₆, CHR₆—O, NR₆—CH₂, CH₂—NR₆, CHR₆—NR₇ or CR₆R₇, wherein R₆ and/or R₇=H or a lower alkyl, alkene or alkyne having 6 or less C atoms;
wherein Z may be attached to the C ring at positions 5, 6, 7, or 8 and may be attached to more than one of said positions 5, 6, 7, or 8 on the ring, wherein Z may be the same or different;
wherein Z may be zero and R₃ may be directly attached to the C-ring at positions 5, 6, 7, and/or 8;
wherein when the C-ring is saturated or partially saturated the substituted Z or R₃ creates chirality when P=C and R_6 and R_7 are different, then all stereoisomers thereof both separately and as racemic and/or diastereoisomeric mixtures are included;

R_3=H, alkyl, cycloalkyl, aryl, heteroaryl, substituted aryl, substituted heteroaryl, alkylaryl, alkylheteroaryl and substituted saturated or unsaturated alkylheteroaryl and alkylheterocyclic, alkylaryl, p-, m-, o-benzoyl-L-glutamate or 2,5-, 2,4-thienoyl-L-glutamate when the benzene and thiophene ring may or may not have additional substitutions including F, mono-, bi- and tricyclic aryl, heteroaryl or combinations thereof, ring substitutions including biphenyl, bipyridyl or a phenyl-pyridyl or a fused moiety including a quinoline or naphthyl including substituted systems including a 2-chloro,4-biphenyl and tricyclic and substituted tricyclic systems.

2. The method according to claim 1, wherein Y=NH; R_2=H; P=CR_4R_5; R_4=H; R_5=H; X=NH; R_1=a phenyl; Z=0, and R_3=H.

3. The method according to claim 1, wherein Y=NH; R_2=H; P=CR_4R_5; R_4=H; R_5=H; X=NH; R_1=a substituted aryl; Z=0; and R_3=H.

4. The method according to claim 3, wherein the substitution on the aryl is a chloride atom.

5. The method according to claim 1, wherein the route of administration of the compound of formula I is parenteral, oral, or intraperitoneal.

6. The method according to claim 5, wherein the parenteral route of administration is selected from the group consisting of intravenous; intramuscular; interstitial, intraarterial; subcutaneous; intraocular; intracranial; intraventricular; intrasynovial;

transepithelial, including transdermal, pulmonary via inhalation, ophthalmic, sublingual and bucal; topical, including dermal, ocular, rectal and nasal inhalation via insufflation or nebulization.

7. The method according to claim 1, wherein the unit dosage is administered orally in the form of hard or soft shell gelatin capsules, tablets, troches, sachets, lozenges, elixirs, suspensions, syrups, wafers, powders, granules, solutions or emulsions.

8. The method according to claim 6, wherein the nasal administration of the compound of formula I is selected from the group consisting of aerosols, atomizers and nebulizers.

9. The method according to claim 1, wherein said animal or human is afflicted with a proliferative disease or disorder selected from the group consisting of leukemia, non-small cell lung cancer, colon cancer, central nervous system cancer, melanoma, ovarian cancer, renal cancer, prostate cancer, breast cancer; macular degeneration and retinopathies.

10. A method of inhibiting receptor tyrosine kinase(s), dihydrofolate reductase, thymidylate synthase and/or dihydroorotate dehydrogenase activity in an animal or human in need thereof, comprising administering to said animal or human a therapeutically effective amount in unit dosage form of a compound of formula II:

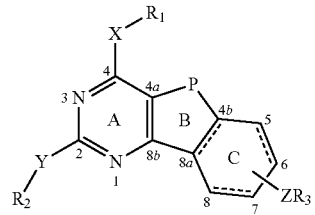

wherein both B and C rings may be completely or partially saturated or unsaturated with respect to bond 4b-8a, 5-6 and 7-8;

X and/or Y=N, NH, O, S, CH_2; P=CR_4R_5 wherein R_4 and R_5=lower alkyl, alkene, alkyne, and all of R_1 and R_2 except that R_4 and R_5 are not each H;

R_1 is H, alkyl, a cycloalkyl having 6 or less carbons, alkene, alkyne, aryl, heteroaryl, substituted aryl, substituted heteroaryl, alkylaryl, alkylheteroaryl, substituted alkylaryl or alkylheteroaryl and R_2=H, alkyl, a cycloalkyl having 6 or less carbon atoms, alkene, alkyne, aryl, heteroaryl, substituted aryl, substituted heteroaryl, alkylaryl, alkylheteroaryl, substituted alkylaryl or alkylheteroaryl;

Z=S, O, NR_6, S—CH_2, CH_2—S, O—CHR_6, CHR_6—O, NR_6—CH_2, CH_2—NR_6, CHR_6—NR_7 or CR_6R_7, wherein R_6 and/or R_7=H or a lower alkyl, alkene or alkyne having 6 or less C atoms;

wherein Z may be attached to the C ring at positions 5, 6, 7 or 8 and may be attached to more than one of said positions 5, 6, 7, or 8 on the ring wherein Z may be the same or different;

wherein Z may be zero and R_3 may be directly attached to the C-ring at positions 5, 6, 7, and/or 8;

wherein when the C-ring is saturated or partially saturated the substituted Z or R_3 creates chirality when P=C and R_6 and R_7 are different, then all stereoisomers thereof both separately and as racemic and/or diastereoisomeric mixtures are included;

R_3=H, alkyl, cycloalkyl, aryl, heteroaryl, substituted aryl, substituted heteroaryl, alkylaryl, alkylheteroaryl and substituted saturated or unsaturated alkylheteroaryl and alkylheterocyclic, alkylaryl, p-, m-, o-benzoyl-L-glutamate or 2,5-, 2,4-thienoyl-L-glutamate when the benzene and thiophene ring may or may not have additional substitutions including F, mono-, bi- and tricyclic aryl, heteroaryl or combinations thereof, ring substitutions including biphenyl, bipyidyl or a phenyl-pyridyl or a fused moiety including a quinoline or naphthyl including substituted systems including a 2-chloro,4-biphenyl and tricyclic and substituted tricyclic systems.

11. The method according to claim 10, wherein Y=NH; R_2=H; X=NH; R_1=phenyl; Z=0; and R_3=H.

12. The method according to claim 10, wherein the route of administration of the compound of formula II is parenteral, oral or intraperitoneal.

13. The method according to claim 12, wherein the parenteral route of administration is selected from the group consisting of intravenous; intramuscular; interstitial, intraarterial; subcutaneous; intraocular; intracranial; intraventricular; intrasynovial; transepithelial, including transdermal, pulmonary via inhalation, ophthalmic, sublingual and bucal; topical, including dermal, ocular, rectal and nasal inhalation via insufflation or nebulization.

14. The method according to claim 13, wherein the nasal administration of the compound of formula II is selected from the group consisting of aerosols, atomizers and nebulizers.

15. The method according to claim 10, wherein the unit dosage is administered orally in the form of hard or soft shell gelatin capsules, tablets, troches, sachets, lozenges, elixirs, suspensions, syrups, wafers, powders, granules, solutions or emulsions.

16. The method according to claim 10, wherein said animal or human is afflicted with a proliferative disease or disorder selected from the group consisting of leukemia, non-small cell lung cancer, colon cancer, central nervous system cancer, melanoma, ovarian cancer, renal cancer, prostate cancer, breast cancer; macular degeneration and retinopathies.

* * * * *